(12) United States Patent
Williamson et al.

(10) Patent No.: US 7,888,007 B2
(45) Date of Patent: Feb. 15, 2011

(54) CANCER ASSOCIATED PLEXIN B1 MUTATIONS

(75) Inventors: Magali Williamson, London (GB); John Masters, London (GB)

(73) Assignee: The Prostate Cancer Research Centre, London (GB)

( * ) Notice: Subject to any disclaimer, the term of this patent is extended or adjusted under 35 U.S.C. 154(b) by 490 days.

(21) Appl. No.: 10/536,804

(22) PCT Filed: Nov. 28, 2003

(86) PCT No.: PCT/GB03/05223

§ 371 (c)(1),
(2), (4) Date: Nov. 10, 2005

(87) PCT Pub. No.: WO2004/050914

PCT Pub. Date: Jun. 17, 2004

(65) Prior Publication Data

US 2006/0127908 A1    Jun. 15, 2006

(30) Foreign Application Priority Data

Nov. 28, 2002   (GB) .................................. 0227908.1

(51) Int. Cl.
   *C12Q 1/68* (2006.01)
   *G01N 33/574* (2006.01)
   *C07H 21/02* (2006.01)
   *C07H 21/04* (2006.01)

(52) U.S. Cl. .................. 435/6; 435/7.21; 435/7.23; 536/23.1; 536/23.5

(58) Field of Classification Search .................. None
See application file for complete search history.

(56) References Cited

U.S. PATENT DOCUMENTS

| 2004/0005563 A1* | 1/2004 | Mack et al. ..................... 435/6 |
| 2005/0047996 A1* | 3/2005 | Vogelstein et al. ......... 424/1.49 |
| 2006/0019256 A1* | 1/2006 | Clarke et al. ..................... 435/6 |

FOREIGN PATENT DOCUMENTS

| WO | WO 01/54477 | 8/2001 |
| WO | WO 02/31209 | 4/2002 |
| WO | WO 02/059377 | 8/2002 |
| WO | WO 02/068579 A2 * | 9/2002 |
| WO | WO 03/031930 | 4/2003 |

OTHER PUBLICATIONS

Taber's Cyclopedic Medical Dictionary (1985, F.A. Davis Company, Philadelphia, p. 274).*
Busken, C et al, (Digestive Disease Week Abstracts and Itinerary Planner, 2003, abstract No:850).*
Kaiser (Science, 2006, 313, 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. Chemotherapy of Cancer; Second edition; John Wiley & Sons : New York, 1981; appendix C.*
Benedict et al (J. Exp. Medicine, 2001, 193(1) 89-99).*
Jiang et al (J. Biol. Chem., 2003, 278(7) 4763-4769).*
Matsushita et al (FEBS Letters, 1999, vol. 443, pp. 348-352).*
Freshney (Culture of Animal Cells, A Manual of Basic Technique, Alan R. Liss, Inc., 1983, New York, p. 4).*
Dermer (Bio/Technology, 1994, 12: 320).*
Drexler et al (Leukemia and Lymphoma, 1993, 9:1-25).*
Zellner et al (Clin. Can. Res., 1998, 4:1797-1802).*
Zips et al (In vivo, 2005, 19:1-7).*
Giordano S. et al, "The semaphoring 4D receptor controls invasive growth by coupling with Met." Nat Cell Biol. 2002 Sep; 4(9):720-724.
Aurandt et al, Proceedings of the National Academy of Sciences, Sep. 17, 2002, vol. 99, No. 19, pp. 12085-12090.
Haga et al, Journal of Human Genetics, 2002, vol. 47, No. 11, pp. 605-610.
Buetow et al, Nature Genetics, Mar. 1999, vol. 21, pp. 323-325.
Stratton et al, Nature 458:719-724, 2009 "The Cancer Genome".

* cited by examiner

*Primary Examiner*—Peter J Reddig
(74) *Attorney, Agent, or Firm*—Nixon & Vanderhye P.C.

(57) ABSTRACT

The present inventors have identified cancer associated mutations in plexinB1, which is a transmembrane receptor that mediates semaphorin signaling. The frequency of plexinB1 mutations, in particular in prostate and breast cancer, indicates that plexinB1 may be useful in the screening and diagnosis of cancer and as a drug target in the development of anti-cancer therapeutics.

5 Claims, 17 Drawing Sheets

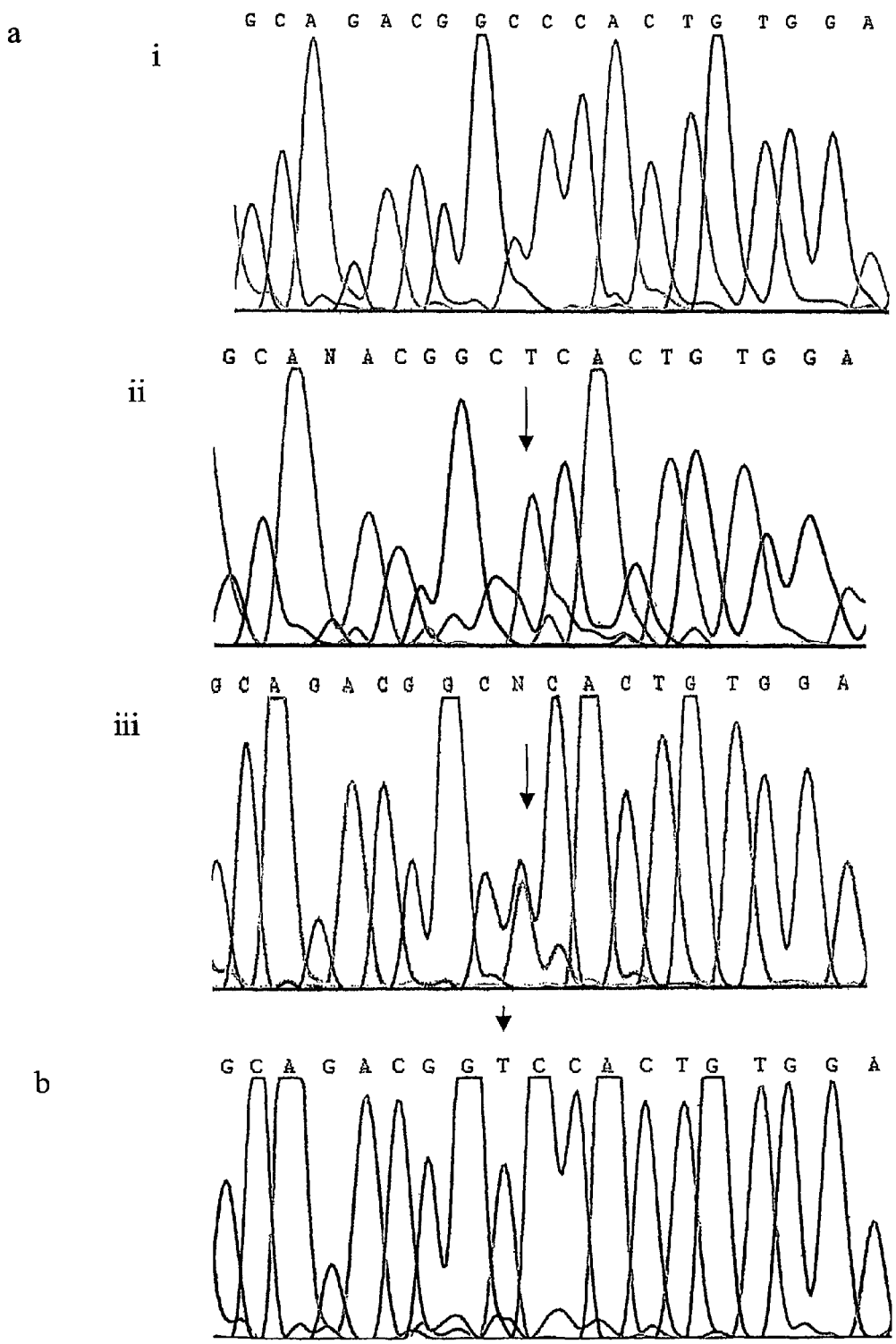

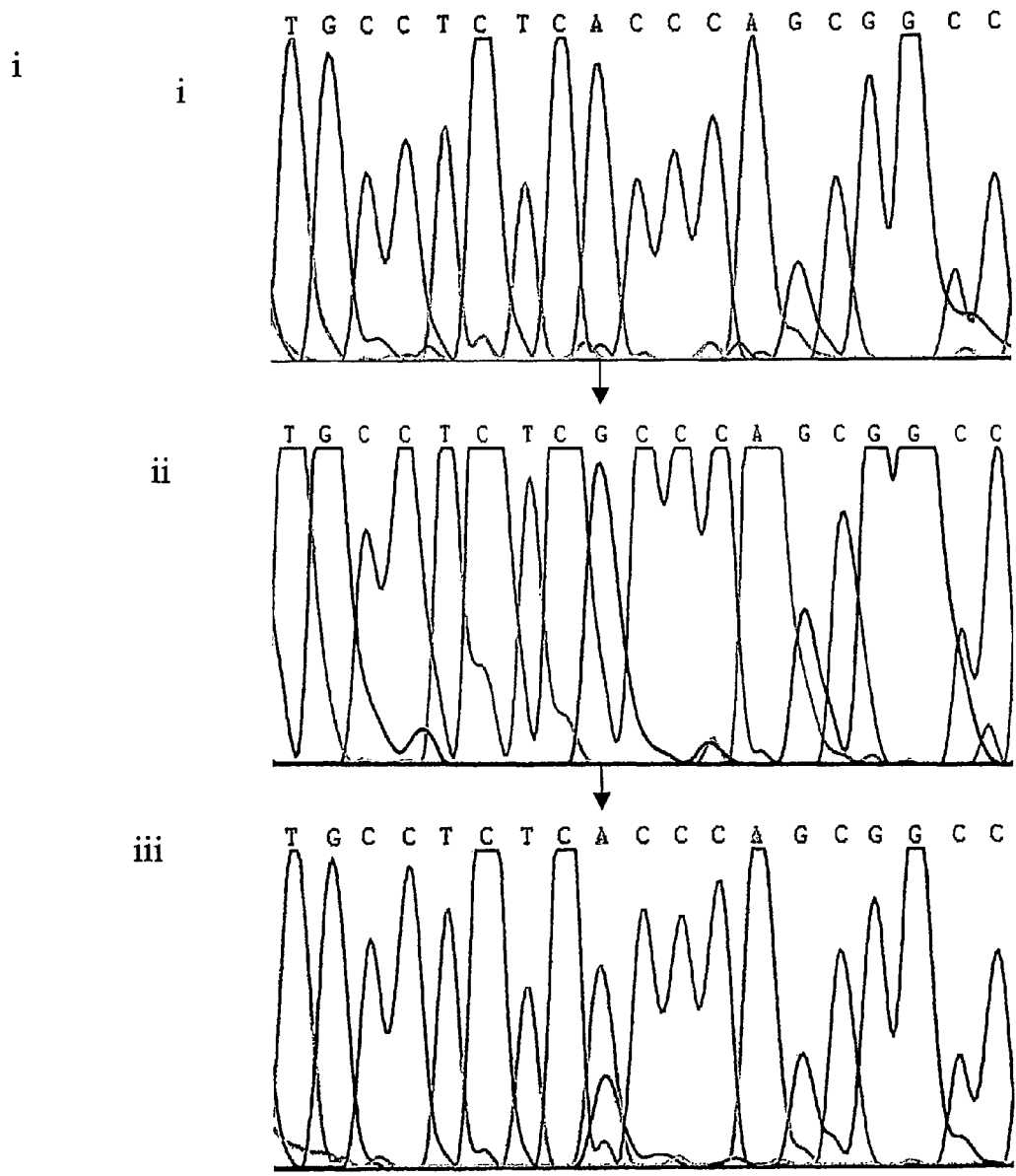

Figure 5

SEQUENCE LISTING

<160> NUMBER OF SEQ ID NOS: 112

<210> SEQ ID NO 1
<211> LENGTH: 19
<212> TYPE: DNA
<213> ORGANISM: Homo sapiens

<400> SEQUENCE: 1
gcagacggcc cactgtgga                                                  19

<210> SEQ ID NO 2
<211> LENGTH: 19
<212> TYPE: DNA
<213> ORGANISM: Homo sapiens
<220> FEATURE:
<221> NAME/KEY: modified_base
<222> LOCATION: (4)..(4)
<223> OTHER INFORMATION: a, c, t, g, unknown or other

<400> SEQUENCE: 2
gcanacggct cactgtgga                                                  19

<210> SEQ ID NO 3
<211> LENGTH: 19
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other

```
<400> SEQUENCE: 3
gcagacggcn cactgtgga                                              19

<210> SEQ ID NO 4
<211> LENGTH: 19
<212> TYPE: DNA
<213> ORGANISM: Homo sapiens

<400> SEQUENCE: 4
gcagacggtc cactgtgga                                              19

<210> SEQ ID NO 5
<211> LENGTH: 19
<212> TYPE: DNA
<213> ORGANISM: Homo sapiens

<400> SEQUENCE: 5
tgccccagcc cttgctcca                                              19

<210> SEQ ID NO 6
<211> LENGTH: 19
<212> TYPE: DNA
<213> ORGANISM: Homo sapiens

<400> SEQUENCE: 6
tgccccagcc tttgctcca                                              19

<210> SEQ ID NO 7
<211> LENGTH: 19
<212> TYPE: DNA
<213> ORGANISM: Homo sapiens

<400> SEQUENCE: 7
tgtctgtata ccttcgtga                                              19

<210> SEQ ID NO 8
<211> LENGTH: 19
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other

<400> SEQUENCE: 8
tgtctgtatn ccttcgtga                                              19

<210> SEQ ID NO 9
<211> LENGTH: 19
<212> TYPE: DNA
<213> ORGANISM: Homo sapiens

<400> SEQUENCE: 9
tccctcgaaa gagcatgta                                              19

<210> SEQ ID NO 10
<211> LENGTH: 19
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other

<400> SEQUENCE: 10
```

-continued

```
tccctcgaan gagcatgta                                        19

<210> SEQ ID NO 11
<211> LENGTH: 19
<212> TYPE: DNA
<213> ORGANISM: Homo sapiens

<400> SEQUENCE: 11
ccaaatacac cttgaacga                                        19

<210> SEQ ID NO 12
<211> LENGTH: 19
<212> TYPE: DNA
<213> ORGANISM: Homo sapiens

<400> SEQUENCE: 12
ccaaatacat cttgaacga                                        19

<210> SEQ ID NO 13
<211> LENGTH: 19
<212> TYPE: DNA
<213> ORGANISM: Homo sapiens

<400> SEQUENCE: 13
acaccttgaa cgacaaccg                                        19

<210> SEQ ID NO 14
<211> LENGTH: 19
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other

<400> SEQUENCE: 14
acaccttgan cgacaaccg                                        19

<210> SEQ ID NO 15
<211> LENGTH: 19
<212> TYPE: DNA
<213> ORGANISM: Homo sapiens

<400> SEQUENCE: 15
gactgtgaca ccatctccc                                        19

<210> SEQ ID NO 16
<211> LENGTH: 19
<212> TYPE: DNA
<213> ORGANISM: Homo sapiens

<400> SEQUENCE: 16
tgcctctcac ccagcggcc                                        19

<210> SEQ ID NO 17
<211> LENGTH: 19
<212> TYPE: DNA
<213> ORGANISM: Homo sapiens

<400> SEQUENCE: 17
tgcctctcgc ccagcggcc                                        19

<210> SEQ ID NO 18
```

```
<211> LENGTH: 19
<212> TYPE: DNA
<213> ORGANISM: Homo sapiens

<400> SEQUENCE: 18
cccagcggcc agaccctcg                                                19

<210> SEQ ID NO 19
<211> LENGTH: 19
<212> TYPE: DNA
<213> ORGANISM: Homo sapiens
<220> FEATURE:
<221> NAME/KEY: modified_base
<222> LOCATION: (12)..(12)
<223> OTHER INFORMATION: a, c, t, g, unknown or other

<400> SEQUENCE: 19
cccagcggtc anaccctcg                                                19

<210> SEQ ID NO 20
<211> LENGTH: 19
<212> TYPE: DNA
<213> ORGANISM: Homo sapiens

<400> SEQUENCE: 20
cccagcggtc agaccctcg                                                19

<210> SEQ ID NO 21
<211> LENGTH: 19
<212> TYPE: DNA
<213> ORGANISM: Homo sapiens

<400> SEQUENCE: 21
ccctcgcacc cttgatgtt                                                19

<210> SEQ ID NO 22
<211> LENGTH: 19
<212> TYPE: DNA
<213> ORGANISM: Homo sapiens

<400> SEQUENCE: 22
ccctcgcgcc cttgatgtt                                                19

<210> SEQ ID NO 23
<211> LENGTH: 19
<212> TYPE: DNA
<213> ORGANISM: Homo sapiens

<400> SEQUENCE: 23
aaagaatgag gtgcccggc                                                19

<210> SEQ ID NO 24
<211> LENGTH: 20
<212> TYPE: DNA
<213> ORGANISM: Homo sapiens

<400> SEQUENCE: 24
aattgaatgg ggtgcccggc                                               20

<210> SEQ ID NO 25
<211> LENGTH: 19
<212> TYPE: DNA
<213> ORGANISM: Homo sapiens
<220> FEATURE:
<221> NAME/KEY: modified_base
```

-continued

```
<222> LOCATION: (9)..(9)
<223> OTHER INFORMATION: a, c, t, g, unknown or other

<400> SEQUENCE: 25
aaagaatgng gtgcccggc                                              19

<210> SEQ ID NO 26
<211> LENGTH: 19
<212> TYPE: DNA
<213> ORGANISM: Homo sapiens

<400> SEQUENCE: 26
ccccgccccg aaggctgcc                                              19

<210> SEQ ID NO 27
<211> LENGTH: 19
<212> TYPE: DNA
<213> ORGANISM: Homo sapiens

<400> SEQUENCE: 27
ccccgcccca aaggctgcc                                              19

<210> SEQ ID NO 28
<211> LENGTH: 13
<212> TYPE: PRT
<213> ORGANISM: Homo sapiens

<400> SEQUENCE: 28

Glu Ser Arg Arg Pro Thr Val Glu Gln Gly Leu Gly Gln
1               5                   10

<210> SEQ ID NO 29
<211> LENGTH: 13
<212> TYPE: PRT
<213> ORGANISM: Homo sapiens

<400> SEQUENCE: 29

Glu Ser Arg Arg Leu Thr Val Glu Gln Gly Leu Gly Gln
1               5                   10

<210> SEQ ID NO 30
<211> LENGTH: 13
<212> TYPE: PRT
<213> ORGANISM: Homo sapiens

<400> SEQUENCE: 30

Glu Ser Arg Arg Ser Thr Val Glu Gln Gly Leu Gly Gln
1               5                   10

<210> SEQ ID NO 31
<211> LENGTH: 13
<212> TYPE: PRT
<213> ORGANISM: Homo sapiens

<400> SEQUENCE: 31

Glu Ser Arg Arg Pro Thr Val Glu Gln Thr Leu Gly Gln
1               5                   10

<210> SEQ ID NO 32
<211> LENGTH: 13
<212> TYPE: PRT
<213> ORGANISM: Mus musculus

<400> SEQUENCE: 32
```

-continued

Asp Ser Arg Arg Pro Thr Val Glu Gln Gly Leu Gly Gln
1               5                   10

<210> SEQ ID NO 33
<211> LENGTH: 13
<212> TYPE: PRT
<213> ORGANISM: Drosophila melanogaster

<400> SEQUENCE: 33

Gly Ser Pro Gln Thr Asn Tyr Asp Ala Ala Met Val Gln
1               5                   10

<210> SEQ ID NO 34
<211> LENGTH: 13
<212> TYPE: PRT
<213> ORGANISM: Caenothabditis elegans

<400> SEQUENCE: 34

Pro Ser Leu Ala Arg Thr Leu Pro Val Thr Leu Ala Gln
1               5                   10

<210> SEQ ID NO 35
<211> LENGTH: 13
<212> TYPE: PRT
<213> ORGANISM: Homo sapiens

<400> SEQUENCE: 35

Asp Gly His Cys Ala Thr Val Arg Gln Gly Leu Thr Gln
1               5                   10

<210> SEQ ID NO 36
<211> LENGTH: 13
<212> TYPE: PRT
<213> ORGANISM: Homo sapiens

<400> SEQUENCE: 36

Gly Asn Gly Gln Gln His Val Glu Lys Ala Leu Lys Leu
1               5                   10

<210> SEQ ID NO 37
<211> LENGTH: 9
<212> TYPE: PRT
<213> ORGANISM: Homo sapiens

<400> SEQUENCE: 37

Ile Cys Leu Tyr Thr Phe Val Arg Asp
1               5

<210> SEQ ID NO 38
<211> LENGTH: 9
<212> TYPE: PRT
<213> ORGANISM: Homo sapiens

<400> SEQUENCE: 38

Ile Cys Leu Tyr Ala Phe Val Arg Asp
1               5

<210> SEQ ID NO 39
<211> LENGTH: 9
<212> TYPE: PRT
<213> ORGANISM: Drosophila melanogaster

<400> SEQUENCE: 39

Ile Cys Met Tyr Asp Tyr Leu Lys Glu
1               5

```
<210> SEQ ID NO 40
<211> LENGTH: 9
<212> TYPE: PRT
<213> ORGANISM: Caenothabditis elegans

<400> SEQUENCE: 40

Ile Cys Leu Tyr Ser His Leu Thr Pro
1               5

<210> SEQ ID NO 41
<211> LENGTH: 9
<212> TYPE: PRT
<213> ORGANISM: Homo sapiens

<400> SEQUENCE: 41

Ile Cys Leu Tyr Ala Phe Leu Arg Glu
1               5

<210> SEQ ID NO 42
<211> LENGTH: 9
<212> TYPE: PRT
<213> ORGANISM: Homo sapiens

<400> SEQUENCE: 42

Ile Cys Leu Tyr Gln Tyr Leu Lys Asp
1               5

<210> SEQ ID NO 43
<211> LENGTH: 9
<212> TYPE: PRT
<213> ORGANISM: Homo sapiens

<400> SEQUENCE: 43

Phe Leu Leu His Lys Phe Leu Lys Glu
1               5

<210> SEQ ID NO 44
<211> LENGTH: 9
<212> TYPE: PRT
<213> ORGANISM: Homo sapiens

<400> SEQUENCE: 44

Leu Tyr Met Leu Phe Arg Gly Ile Lys
1               5

<210> SEQ ID NO 45
<211> LENGTH: 9
<212> TYPE: PRT
<213> ORGANISM: Homo sapiens

<400> SEQUENCE: 45

Leu Tyr Met Leu Ile Arg Gly Ile Lys
1               5

<210> SEQ ID NO 46
<211> LENGTH: 9
<212> TYPE: PRT
<213> ORGANISM: Drosophila melanogaster

<400> SEQUENCE: 46

Leu Phe Leu Leu Phe Lys Ala Ile Lys
1               5
```

<210> SEQ ID NO 47
<211> LENGTH: 8
<212> TYPE: PRT
<213> ORGANISM: Caenothabditis elegans

<400> SEQUENCE: 47

Phe Tyr Leu Tyr Lys Ala Leu Gln
1               5

<210> SEQ ID NO 48
<211> LENGTH: 9
<212> TYPE: PRT
<213> ORGANISM: Homo sapiens

<400> SEQUENCE: 48

Leu Tyr Met Leu Phe Arg Ala Ile Gln
1               5

<210> SEQ ID NO 49
<211> LENGTH: 9
<212> TYPE: PRT
<213> ORGANISM: Homo sapiens

<400> SEQUENCE: 49

Leu Tyr Lys Leu Phe Lys Ala Ile Lys
1               5

<210> SEQ ID NO 50
<211> LENGTH: 15
<212> TYPE: PRT
<213> ORGANISM: Homo sapiens

<400> SEQUENCE: 50

Asp Ser Val Thr Gly Lys Ala Lys Tyr Thr Leu Asn Asp Asn Arg
1               5                   10                  15

<210> SEQ ID NO 51
<211> LENGTH: 15
<212> TYPE: PRT
<213> ORGANISM: Homo sapiens

<400> SEQUENCE: 51

Asp Ser Val Thr Ser Lys Ala Lys Tyr Thr Leu Asn Asp Asn Arg
1               5                   10                  15

<210> SEQ ID NO 52
<211> LENGTH: 15
<212> TYPE: PRT
<213> ORGANISM: Homo sapiens

<400> SEQUENCE: 52

Asp Ser Val Thr Gly Lys Thr Lys Tyr Thr Leu Asn Asp Asn Arg
1               5                   10                  15

<210> SEQ ID NO 53
<211> LENGTH: 15
<212> TYPE: PRT
<213> ORGANISM: Homo sapiens

<400> SEQUENCE: 53

Asp Ser Val Thr Gly Lys Ala Lys Tyr Ile Leu Asn Asp Asn Arg
1               5                   10                  15

<210> SEQ ID NO 54
<211> LENGTH: 15

```
<212> TYPE: PRT
<213> ORGANISM: Homo sapiens

<400> SEQUENCE: 54

Asp Ser Val Thr Gly Lys Ala Lys Tyr Thr Leu Ser Asp Asn Arg
1               5                   10                  15

<210> SEQ ID NO 55
<211> LENGTH: 15
<212> TYPE: PRT
<213> ORGANISM: Drosophila melanogaster

<400> SEQUENCE: 55

Asp Ala Ile Thr Asn Asp Ala Arg Tyr Ser Leu Ser Glu Glu Arg
1               5                   10                  15

<210> SEQ ID NO 56
<211> LENGTH: 15
<212> TYPE: PRT
<213> ORGANISM: Caenothabditis elegans

<400> SEQUENCE: 56

Asp Ala Val Thr Gly Asp Ala Arg Tyr Thr Ile Asn Glu Ala Lys
1               5                   10                  15

<210> SEQ ID NO 57
<211> LENGTH: 15
<212> TYPE: PRT
<213> ORGANISM: Homo sapiens

<400> SEQUENCE: 57

Asp Ala Val Thr Gly Lys Ala Lys Arg Thr Ile Asn Asp Ser Arg
1               5                   10                  15

<210> SEQ ID NO 58
<211> LENGTH: 15
<212> TYPE: PRT
<213> ORGANISM: Homo sapiens

<400> SEQUENCE: 58

Asp Ala Val Gln Lys Lys Ala Lys Tyr Thr Leu Asn Asp Thr Gly
1               5                   10                  15

<210> SEQ ID NO 59
<211> LENGTH: 15
<212> TYPE: PRT
<213> ORGANISM: Homo sapiens

<400> SEQUENCE: 59

Asp Ala Ile Thr Gly Glu Ala Arg Tyr Ser Leu Ser Glu Asp Lys
1               5                   10                  15

<210> SEQ ID NO 60
<211> LENGTH: 8
<212> TYPE: PRT
<213> ORGANISM: Homo sapiens

<400> SEQUENCE: 60

Leu Asp Cys Asp Thr Ile Ser Gln
1               5

<210> SEQ ID NO 61
<211> LENGTH: 8
<212> TYPE: PRT
<213> ORGANISM: Homo sapiens
```

```
<400> SEQUENCE: 61

Leu Asp Cys Asp Ala Ile Ser Gln
1               5

<210> SEQ ID NO 62
<211> LENGTH: 8
<212> TYPE: PRT
<213> ORGANISM: Mus musculus

<400> SEQUENCE: 62

Leu Asp Thr Asp Thr Ile Ser Gln
1               5

<210> SEQ ID NO 63
<211> LENGTH: 8
<212> TYPE: PRT
<213> ORGANISM: Drosophila melanogaster

<400> SEQUENCE: 63

Asn Asp Trp Asp Thr Ile Ser Gln
1               5

<210> SEQ ID NO 64
<211> LENGTH: 8
<212> TYPE: PRT
<213> ORGANISM: Caenothabditis elegans

<400> SEQUENCE: 64

His Ala Cys Asp Ala Ile Cys Gln
1               5

<210> SEQ ID NO 65
<211> LENGTH: 8
<212> TYPE: PRT
<213> ORGANISM: Homo sapiens

<400> SEQUENCE: 65

Leu Asp Thr Asp Thr Ile Thr Gln
1               5

<210> SEQ ID NO 66
<211> LENGTH: 8
<212> TYPE: PRT
<213> ORGANISM: Homo sapiens

<400> SEQUENCE: 66

Leu Asn Cys Asp Thr Ile Ser Gln
1               5

<210> SEQ ID NO 67
<211> LENGTH: 8
<212> TYPE: PRT
<213> ORGANISM: Homo sapiens

<400> SEQUENCE: 67

Leu Asn Cys Asp Thr Ile Thr Gln
1               5

<210> SEQ ID NO 68
<211> LENGTH: 8
<212> TYPE: PRT
<213> ORGANISM: Homo sapiens

<400> SEQUENCE: 68
```

```
Leu Asp Cys Asp Thr Val Thr Gln
1               5

<210> SEQ ID NO 69
<211> LENGTH: 15
<212> TYPE: PRT
<213> ORGANISM: Homo sapiens

<400> SEQUENCE: 69

Gly Val Pro Leu Thr Gln Arg Pro Asp Pro Arg Thr Leu Asp Val
1               5                   10                  15

<210> SEQ ID NO 70
<211> LENGTH: 15
<212> TYPE: PRT
<213> ORGANISM: Homo sapiens

<400> SEQUENCE: 70

Gly Val Pro Leu Ala Gln Arg Pro Asp Pro Arg Thr Leu Asp Val
1               5                   10                  15

<210> SEQ ID NO 71
<211> LENGTH: 15
<212> TYPE: PRT
<213> ORGANISM: Homo sapiens

<400> SEQUENCE: 71

Gly Val Pro Leu Thr Gln Arg Ser Asp Pro Arg Thr Leu Asp Val
1               5                   10                  15

<210> SEQ ID NO 72
<211> LENGTH: 15
<212> TYPE: PRT
<213> ORGANISM: Homo sapiens

<400> SEQUENCE: 72

Gly Val Pro Leu Thr Gln Arg Pro Asp Pro Arg Ala Leu Asp Val
1               5                   10                  15

<210> SEQ ID NO 73
<211> LENGTH: 15
<212> TYPE: PRT
<213> ORGANISM: Mus musculus

<400> SEQUENCE: 73

Gly Val Pro Leu Ala Gln Arg Pro Asp Ser Cys Thr Leu Asp Val
1               5                   10                  15

<210> SEQ ID NO 74
<211> LENGTH: 15
<212> TYPE: PRT
<213> ORGANISM: Drosophila melanogaster

<400> SEQUENCE: 74

Asn Thr Pro Phe Ser Met Lys Pro Ser Val Asn Glu Leu Asp Leu
1               5                   10                  15

<210> SEQ ID NO 75
<211> LENGTH: 15
<212> TYPE: PRT
<213> ORGANISM: Caenothabditis elegans

<400> SEQUENCE: 75

Glu Thr Pro Leu Ser Gln Arg Pro Arg Ile Thr Gln Phe Glu Leu
```

```
                1               5               10              15
```

<210> SEQ ID NO 76
<211> LENGTH: 15
<212> TYPE: PRT
<213> ORGANISM: Homo sapiens

<400> SEQUENCE: 76

```
Gly Thr Pro Phe Ser Gln Arg Pro Ser Val His Ala Leu Asp Leu
1               5                   10                  15
```

<210> SEQ ID NO 77
<211> LENGTH: 15
<212> TYPE: PRT
<213> ORGANISM: Homo sapiens

<400> SEQUENCE: 77

```
Gly Gln Pro Leu Thr Cys Trp Pro Arg Pro Asp Ser Val Val Leu
1               5                   10                  15
```

<210> SEQ ID NO 78
<211> LENGTH: 15
<212> TYPE: PRT
<213> ORGANISM: Homo sapiens

<400> SEQUENCE: 78

```
Asn Val Pro Tyr Ser Gln Arg Pro Arg Ala Val Asp Met Asp Ala
1               5                   10                  15
```

<210> SEQ ID NO 79
<211> LENGTH: 15
<212> TYPE: PRT
<213> ORGANISM: Homo sapiens

<400> SEQUENCE: 79

```
Gly Val Pro Tyr Ser Gln Arg Pro Lys Ala Ala Asp Met Asp Leu
1               5                   10                  15
```

<210> SEQ ID NO 80
<211> LENGTH: 9
<212> TYPE: PRT
<213> ORGANISM: Homo sapiens

<400> SEQUENCE: 80

```
Val Ala Gly His Leu Ile Leu Ser Asp
1               5
```

<210> SEQ ID NO 81
<211> LENGTH: 9
<212> TYPE: PRT
<213> ORGANISM: Homo sapiens

<400> SEQUENCE: 81

```
Val Ala Gly His Pro Ile Leu Ser Asp
1               5
```

<210> SEQ ID NO 82
<211> LENGTH: 9
<212> TYPE: PRT
<213> ORGANISM: Homo sapiens

<400> SEQUENCE: 82

```
Val Ala Gly His Phe Ile Leu Ser Asp
1               5
```

```
<210> SEQ ID NO 83
<211> LENGTH: 9
<212> TYPE: PRT
<213> ORGANISM: Drosophila melanogaster

<400> SEQUENCE: 83

Arg Gly Gly His Leu Thr Leu Gln Asp
1               5

<210> SEQ ID NO 84
<211> LENGTH: 9
<212> TYPE: PRT
<213> ORGANISM: Caenothabditis elegans

<400> SEQUENCE: 84

Lys Arg Gly Asp Val Lys Leu Thr Asp
1               5

<210> SEQ ID NO 85
<211> LENGTH: 8
<212> TYPE: PRT
<213> ORGANISM: Homo sapiens

<400> SEQUENCE: 85

Ala Gly His Leu Thr Leu Ser Asp
1               5

<210> SEQ ID NO 86
<211> LENGTH: 8
<212> TYPE: PRT
<213> ORGANISM: Homo sapiens

<400> SEQUENCE: 86

Ser Thr Ala Gln Ile Leu Ser Asp
1               5

<210> SEQ ID NO 87
<211> LENGTH: 9
<212> TYPE: PRT
<213> ORGANISM: Homo sapiens

<400> SEQUENCE: 87

Arg Ala Ile Arg Val Val Leu Gln Asp
1               5

<210> SEQ ID NO 88
<211> LENGTH: 9
<212> TYPE: PRT
<213> ORGANISM: Homo sapiens

<400> SEQUENCE: 88

Arg Met Ala Arg Ile Ile Leu Gln Asp
1               5

<210> SEQ ID NO 89
<211> LENGTH: 10
<212> TYPE: PRT
<213> ORGANISM: Homo sapiens

<400> SEQUENCE: 89

Arg Arg Gly Ser Leu Arg Gly Gly Glu Arg
1               5                   10

<210> SEQ ID NO 90
```

```
<211> LENGTH: 10
<212> TYPE: PRT
<213> ORGANISM: Homo sapiens

<400> SEQUENCE: 90

Arg Arg Gly Ser Leu Trp Gly Gly Glu Arg
1               5                   10

<210> SEQ ID NO 91
<211> LENGTH: 10
<212> TYPE: PRT
<213> ORGANISM: Drosophila melanogaster

<400> SEQUENCE: 91

Asn Asn Ser Val Leu Ser Gly Gly Ser Pro
1               5                   10

<210> SEQ ID NO 92
<211> LENGTH: 10
<212> TYPE: PRT
<213> ORGANISM: Homo sapiens

<400> SEQUENCE: 92

Cys Cys Ser Ser Leu Arg Glu Arg Glu Pro
1               5                   10

<210> SEQ ID NO 93
<211> LENGTH: 8
<212> TYPE: PRT
<213> ORGANISM: Homo sapiens

<400> SEQUENCE: 93

Arg Arg Gly Ser Val Lys Glu Lys
1               5

<210> SEQ ID NO 94
<211> LENGTH: 4
<212> TYPE: PRT
<213> ORGANISM: Homo sapiens

<400> SEQUENCE: 94

Arg Arg Gly Ser
1

<210> SEQ ID NO 95
<211> LENGTH: 19
<212> TYPE: DNA
<213> ORGANISM: Homo sapiens

<400> SEQUENCE: 95
cacagtgggc cgtctgctc                                              19

<210> SEQ ID NO 96
<211> LENGTH: 19
<212> TYPE: DNA
<213> ORGANISM: Homo sapiens

<400> SEQUENCE: 96
cacagtgagc cgtctgctc                                              19

<210> SEQ ID NO 97
<211> LENGTH: 19
<212> TYPE: DNA
<213> ORGANISM: Homo sapiens
<220> FEATURE:
```

-continued

```
<221> NAME/KEY: modified_base
<222> LOCATION: (9)..(9)
<223> OTHER INFORMATION: a, c, t, g, unknown or other

<400> SEQUENCE: 97
cacagtggnc cgtctgctc                                                 19

<210> SEQ ID NO 98
<211> LENGTH: 19
<212> TYPE: DNA
<213> ORGANISM: Homo sapiens

<400> SEQUENCE: 98
ttggccttgc ctgtcacac                                                 19

<210> SEQ ID NO 99
<211> LENGTH: 19
<212> TYPE: DNA
<213> ORGANISM: Homo sapiens
<220> FEATURE:
<221> NAME/KEY: modified_base
<222> LOCATION: (11)..(11)
<223> OTHER INFORMATION: a, c, t, g, unknown or other

<400> SEQUENCE: 99
ttggccttgc ntgtcacac                                                 19

<210> SEQ ID NO 100
<211> LENGTH: 19
<212> TYPE: DNA
<213> ORGANISM: Homo sapiens

<400> SEQUENCE: 100
tgtatttggc cttgcctgt                                                 19

<210> SEQ ID NO 101
<211> LENGTH: 19
<212> TYPE: DNA
<213> ORGANISM: Homo sapiens

<400> SEQUENCE: 101
tgtatttggt cttgcctgt                                                 19

<210> SEQ ID NO 102
<211> LENGTH: 19
<212> TYPE: DNA
<213> ORGANISM: Homo sapiens

<400> SEQUENCE: 102
aaagaatgag gtgcccggc                                                 19

<210> SEQ ID NO 103
<211> LENGTH: 19
<212> TYPE: DNA
<213> ORGANISM: Homo sapiens

<400> SEQUENCE: 103
aaagaatgaa gtgcccggc                                                 19

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
```

```
              primer

<400> SEQUENCE: 104
gtccatctgt ctgtatgcct tcgtgagggt gag                                    33

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctcaccctca cgaaggcata cagacagatg gac                                    33

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggagtgcctc tcgcccagcg gccagaccct cg                                     32

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cgagggtctg gccgctgggc gagaggcact cc                                     32

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggtggccggg cacccattc tttctgacga gg                                      32

<210> SEQ ID NO 109
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cctcgtcaga aagaatgggg tgcccggcca cc                                     32

<210> SEQ ID NO 110
<211> LENGTH: 4
<212> TYPE: PRT
<213> ORGANISM: Homo sapiens

<400> SEQUENCE: 110
```

Arg Arg Gly Ser
1

<210> SEQ ID NO 111
<211> LENGTH: 2143
<212> TYPE: PRT
<213> ORGANISM: Homo sapiens

<400> SEQUENCE: 111

Ser Ser Arg Pro Cys Gln Val Thr Met Pro Ala Leu Gly Pro Ala Leu
1               5                   10                  15

Leu Gln Ala Leu Trp Ala Gly Trp Val Leu Thr Leu Gln Pro Leu Pro
            20                  25                  30

Pro Thr Ala Phe Thr Pro Asn Gly Thr Tyr Leu Gln His Leu Ala Arg
        35                  40                  45

Asp Pro Thr Ser Gly Thr Leu Tyr Leu Gly Ala Thr Asn Phe Leu Phe
    50                  55                  60

Gln Leu Ser Pro Gly Leu Gln Leu Glu Ala Thr Val Ser Thr Gly Pro
65                  70                  75                  80

Val Leu Asp Ser Arg Asp Cys Leu Pro Pro Val Met Pro Asp Glu Cys
                85                  90                  95

Pro Gln Ala Gln Pro Thr Asn Asn Pro Asn Gln Leu Leu Leu Val Ser
            100                 105                 110

Pro Gly Ala Leu Val Val Cys Gly Ser Val His Gln Gly Val Cys Glu
        115                 120                 125

Gln Arg Arg Leu Gly Gln Leu Glu Gln Leu Leu Leu Arg Pro Glu Arg
    130                 135                 140

Pro Gly Asp Thr Gln Tyr Val Ala Ala Asn Asp Pro Ala Val Ser Thr
145                 150                 155                 160

Val Gly Leu Val Ala Gln Gly Leu Ala Gly Glu Pro Leu Leu Phe Val
                165                 170                 175

Gly Arg Gly Tyr Thr Ser Arg Gly Val Gly Gly Ile Pro Pro Ile
            180                 185                 190

Thr Thr Arg Ala Leu Trp Pro Pro Asp Pro Gln Ala Ala Phe Ser Tyr
        195                 200                 205

Glu Glu Thr Ala Lys Leu Ala Val Gly Arg Leu Ser Glu Tyr Ser His
    210                 215                 220

His Phe Val Ser Ala Phe Ala Arg Gly Ala Ser Ala Tyr Phe Leu Phe
225                 230                 235                 240

Leu Arg Arg Asp Leu Gln Ala Gln Ser Arg Ala Phe Arg Ala Tyr Val
                245                 250                 255

Ser Arg Val Cys Leu Arg Asp Gln His Tyr Tyr Ser Tyr Val Glu Leu
            260                 265                 270

Pro Leu Ala Cys Glu Gly Gly Arg Tyr Gly Leu Ile Gln Ala Ala Ala
        275                 280                 285

Val Ala Thr Ser Arg Glu Val Ala His Gly Glu Val Leu Phe Ala Ala
    290                 295                 300

Phe Ser Ser Ala Ala Pro Pro Thr Val Gly Arg Pro Ser Ala Ala
305                 310                 315                 320

Ala Gly Ala Ser Gly Ala Ser Ala Leu Cys Ala Phe Pro Leu Asp Glu
                325                 330                 335

Val Asp Arg Leu Ala Asn Arg Thr Arg Asp Ala Cys Tyr Thr Arg Glu
            340                 345                 350

Gly Arg Ala Glu Asp Gly Thr Glu Val Ala Tyr Ile Glu Tyr Asp Val
        355                 360                 365

```
Asn Ser Asp Cys Ala Gln Leu Pro Val Asp Thr Leu Asp Ala Tyr Pro
    370                 375                 380

Cys Gly Ser Asp His Thr Pro Ser Pro Met Ala Ser Arg Val Pro Leu
385                 390                 395                 400

Glu Ala Thr Pro Ile Leu Glu Trp Pro Gly Ile Gln Leu Thr Ala Val
                405                 410                 415

Ala Val Thr Met Glu Asp Gly His Thr Ile Ala Phe Leu Gly Asp Ser
            420                 425                 430

Gln Gly Gln Leu His Arg Val Tyr Leu Gly Pro Gly Ser Asp Gly His
                435                 440                 445

Pro Tyr Ser Thr Gln Ser Ile Gln Gln Gly Ser Ala Val Ser Arg Asp
    450                 455                 460

Leu Thr Phe Asp Gly Thr Phe Glu His Leu Tyr Val Met Thr Gln Ser
465                 470                 475                 480

Thr Leu Leu Lys Val Pro Val Ala Ser Cys Ala Gln His Leu Asp Cys
                485                 490                 495

Ala Ser Cys Leu Ala His Arg Asp Pro Tyr Cys Gly Trp Cys Val Leu
            500                 505                 510

Leu Gly Arg Cys Ser Arg Arg Ser Glu Cys Ser Arg Gly Gln Gly Pro
        515                 520                 525

Glu Gln Trp Leu Trp Ser Phe Gln Pro Glu Leu Gly Cys Leu Gln Val
    530                 535                 540

Ala Ala Met Ser Pro Ala Asn Ile Ser Arg Glu Glu Thr Arg Glu Val
545                 550                 555                 560

Phe Leu Ser Val Pro Asp Leu Pro Pro Leu Trp Pro Gly Glu Ser Tyr
                565                 570                 575

Ser Cys His Phe Gly Glu His Gln Ser Pro Ala Leu Leu Thr Gly Ser
            580                 585                 590

Gly Val Met Cys Pro Ser Pro Asp Pro Ser Glu Ala Pro Val Leu Pro
        595                 600                 605

Arg Gly Ala Asp Tyr Val Ser Val Ser Val Glu Leu Arg Phe Gly Ala
    610                 615                 620

Val Val Ile Ala Lys Thr Ser Leu Ser Phe Tyr Asp Cys Val Ala Val
625                 630                 635                 640

Thr Glu Leu Arg Pro Ser Ala Gln Cys Gln Ala Cys Val Ser Ser Arg
                645                 650                 655

Trp Gly Cys Asn Trp Cys Val Trp Gln His Leu Cys Thr His Lys Ala
            660                 665                 670

Ser Cys Asp Ala Gly Pro Met Val Ala Ser His Gln Ser Pro Leu Val
        675                 680                 685

Ser Pro Asp Pro Pro Ala Arg Gly Gly Pro Ser Pro Ser Pro Pro Thr
    690                 695                 700

Ala Pro Lys Ala Leu Ala Thr Pro Ala Pro Asp Thr Leu Pro Val Glu
705                 710                 715                 720

Pro Gly Ala Pro Ser Thr Ala Thr Ala Ser Asp Ile Ser Pro Gly Ala
                725                 730                 735

Ser Pro Ser Leu Leu Ser Pro Trp Gly Pro Trp Ala Gly Ser Gly Ser
            740                 745                 750

Ile Ser Ser Pro Gly Ser Thr Gly Ser Pro Leu His Glu Glu Pro Ser
        755                 760                 765

Pro Pro Ser Pro Gln Asn Gly Pro Gly Thr Ala Val Pro Ala Pro Thr
    770                 775                 780
```

-continued

```
Asp Phe Arg Pro Ser Ala Thr Pro Glu Asp Leu Leu Ala Ser Pro Leu
785                 790                 795                 800

Ser Pro Ser Glu Val Ala Ala Val Pro Ala Asp Pro Gly Pro Glu
            805                 810                 815

Ala Leu His Pro Thr Val Pro Leu Asp Leu Pro Pro Ala Thr Val Pro
        820                 825                 830

Ala Thr Thr Phe Pro Gly Ala Met Gly Ser Val Lys Pro Ala Leu Asp
            835                 840                 845

Trp Leu Thr Arg Glu Gly Gly Glu Leu Pro Glu Ala Asp Glu Trp Thr
    850                 855                 860

Gly Gly Asp Ala Pro Ala Phe Ser Thr Ser Thr Leu Leu Ser Gly Asp
865                 870                 875                 880

Gly Asp Ser Ala Glu Leu Glu Gly Pro Pro Ala Pro Leu Ile Leu Pro
                885                 890                 895

Ser Ser Leu Asp Tyr Gln Tyr Asp Thr Pro Gly Leu Trp Glu Leu Glu
            900                 905                 910

Glu Ala Thr Leu Gly Ala Ser Ser Cys Pro Cys Val Glu Ser Val Gln
        915                 920                 925

Gly Ser Thr Leu Met Pro Val His Val Glu Arg Glu Ile Arg Leu Leu
    930                 935                 940

Gly Arg Asn Leu His Leu Phe Gln Asp Gly Pro Gly Asp Asn Glu Cys
945                 950                 955                 960

Val Met Glu Leu Glu Gly Leu Glu Val Val Glu Ala Arg Val Glu
                965                 970                 975

Cys Glu Pro Pro Pro Asp Thr Gln Cys His Val Thr Cys Gln Gln His
            980                 985                 990

Gln Leu Ser Tyr Glu Ala Leu Gln  Pro Glu Leu Arg Val  Gly Leu Phe
        995                 1000                 1005

Leu Arg Arg Ala Gly Arg Leu  Arg Val Asp Ser Ala  Glu Gly Leu
    1010                1015                1020

His Val Val Leu Tyr Asp Cys  Ser Val Gly His Gly  Asp Cys Ser
    1025                1030                1035

Arg Cys Gln Thr Ala Met Pro  Gln Tyr Gly Cys Val  Trp Cys Glu
    1040                1045                1050

Gly Glu Arg Pro Arg Cys Val  Thr Arg Glu Ala Cys  Gly Glu Ala
    1055                1060                1065

Glu Ala Val Ala Thr Gln Cys  Pro Ala Pro Leu Ile  His Ser Val
    1070                1075                1080

Glu Pro Leu Thr Gly Pro Val  Asp Gly Gly Thr Arg  Val Thr Ile
    1085                1090                1095

Arg Gly Ser Asn Leu Gly Gln  His Val Gln Asp Val  Leu Gly Met
    1100                1105                1110

Val Thr Val Ala Gly Val Pro  Cys Ala Val Asp Ala  Gln Glu Tyr
    1115                1120                1125

Glu Val Ser Ser Ser Leu Val  Cys Ile Thr Gly Ala  Ser Gly Glu
    1130                1135                1140

Glu Val Ala Gly Ala Thr Ala  Val Glu Val Pro Gly  Arg Gly Arg
    1145                1150                1155

Gly Val Ser Glu His Asp Phe  Ala Tyr Gln Asp Pro  Lys Val His
    1160                1165                1170

Ser Ile Phe Pro Ala Arg Gly  Pro Arg Ala Gly Gly  Thr Arg Leu
    1175                1180                1185

Thr Leu Asn Gly Ser Lys Leu  Leu Thr Gly Arg Leu  Glu Asp Ile
```

-continued

```
            1190                1195                1200
Arg Val Val Val Gly Asp Gln Pro Cys His Leu Leu Pro Glu Gln
    1205                1210                1215

Gln Ser Glu Gln Leu Arg Cys Glu Thr Ser Pro Arg Pro Thr Pro
    1220                1225                1230

Ala Thr Leu Pro Val Ala Val Trp Phe Gly Ala Thr Glu Arg Arg
    1235                1240                1245

Leu Gln Arg Gly Gln Phe Lys Tyr Thr Leu Asp Pro Asn Ile Thr
    1250                1255                1260

Ser Ala Gly Pro Thr Lys Ser Phe Leu Ser Gly Gly Arg Glu Ile
    1265                1270                1275

Cys Val Arg Gly Gln Asn Leu Asp Val Val Gln Thr Pro Arg Ile
    1280                1285                1290

Arg Val Thr Val Val Ser Arg Met Leu Gln Pro Ser Gln Gly Leu
    1295                1300                1305

Gly Arg Arg Arg Arg Val Val Pro Glu Thr Ala Cys Ser Leu Gly
    1310                1315                1320

Pro Ser Cys Ser Ser Gln Gln Phe Glu Glu Pro Cys His Val Asn
    1325                1330                1335

Ser Ser Gln Leu Ile Thr Cys Arg Thr Pro Ala Leu Pro Gly Leu
    1340                1345                1350

Pro Glu Asp Pro Trp Val Arg Val Glu Phe Ile Leu Asp Asn Leu
    1355                1360                1365

Val Phe Asp Phe Ala Thr Leu Asn Pro Thr Pro Phe Ser Tyr Glu
    1370                1375                1380

Ala Asp Pro Thr Leu Gln Pro Leu Asn Pro Glu Asp Pro Thr Met
    1385                1390                1395

Pro Phe Arg His Lys Pro Gly Ser Val Phe Ser Val Glu Gly Glu
    1400                1405                1410

Asn Leu Asp Leu Ala Met Ser Lys Glu Glu Val Val Ala Met Ile
    1415                1420                1425

Gly Asp Gly Pro Cys Val Val Lys Thr Leu Thr Arg His His Leu
    1430                1435                1440

Tyr Cys Glu Pro Pro Val Glu Gln Pro Leu Pro Arg His His Ala
    1445                1450                1455

Leu Arg Glu Ala Pro Asp Ser Leu Pro Glu Phe Thr Val Gln Met
    1460                1465                1470

Gly Asn Leu Arg Phe Ser Leu Gly His Val Gln Tyr Asp Gly Glu
    1475                1480                1485

Ser Pro Gly Ala Phe Pro Val Ala Ala Gln Val Gly Leu Gly Val
    1490                1495                1500

Gly Thr Ser Leu Leu Ala Leu Gly Val Ile Ile Ile Val Leu Met
    1505                1510                1515

Tyr Arg Arg Lys Ser Lys Gln Ala Leu Arg Asp Tyr Lys Lys Val
    1520                1525                1530

Gln Ile Gln Leu Glu Asn Leu Glu Ser Ser Val Arg Asp Arg Cys
    1535                1540                1545

Lys Lys Glu Phe Thr Asp Leu Met Thr Glu Met Thr Asp Leu Thr
    1550                1555                1560

Ser Asp Leu Leu Gly Ser Gly Ile Pro Phe Leu Asp Tyr Lys Val
    1565                1570                1575

Tyr Ala Glu Arg Ile Phe Phe Pro Gly His Arg Glu Ser Pro Leu
    1580                1585                1590
```

-continued

```
His Arg Asp Leu Gly Val Pro Glu Ser Arg Arg Pro Thr Val Glu
1595                1600                1605

Gln Gly Leu Gly Gln Leu Ser Asn Leu Leu Asn Ser Lys Leu Phe
1610                1615                1620

Leu Thr Lys Phe Ile His Thr Leu Glu Ser Gln Arg Thr Phe Ser
1625                1630                1635

Ala Arg Asp Arg Ala Tyr Val Ala Ser Leu Leu Thr Val Ala Leu
1640                1645                1650

His Gly Lys Leu Glu Tyr Phe Thr Asp Ile Leu Arg Thr Leu Leu
1655                1660                1665

Ser Asp Leu Val Ala Gln Tyr Val Ala Lys Asn Pro Lys Leu Met
1670                1675                1680

Leu Arg Arg Thr Glu Thr Val Val Glu Lys Leu Leu Thr Asn Trp
1685                1690                1695

Met Ser Ile Cys Leu Tyr Thr Phe Val Arg Asp Ser Val Gly Glu
1700                1705                1710

Pro Leu Tyr Met Leu Phe Arg Gly Ile Lys His Gln Val Asp Lys
1715                1720                1725

Gly Pro Val Asp Ser Val Thr Gly Lys Ala Lys Tyr Thr Leu Asn
1730                1735                1740

Asp Asn Arg Leu Leu Arg Glu Asp Val Glu Tyr Arg Pro Leu Thr
1745                1750                1755

Leu Asn Ala Leu Leu Ala Val Gly Pro Gly Ala Gly Glu Ala Gln
1760                1765                1770

Gly Val Pro Val Lys Val Leu Asp Cys Asp Thr Ile Ser Gln Ala
1775                1780                1785

Lys Glu Lys Met Leu Asp Gln Leu Tyr Lys Gly Val Pro Leu Thr
1790                1795                1800

Gln Arg Pro Asp Pro Arg Thr Leu Asp Val Glu Trp Arg Ser Gly
1805                1810                1815

Val Ala Gly His Leu Ile Leu Ser Asp Glu Asp Val Thr Ser Glu
1820                1825                1830

Val Gln Gly Leu Trp Arg Arg Leu Asn Thr Leu Gln His Tyr Lys
1835                1840                1845

Val Pro Asp Gly Ala Thr Val Ala Leu Val Pro Cys Leu Thr Lys
1850                1855                1860

His Val Leu Arg Glu Asn Gln Asp Tyr Val Pro Gly Glu Arg Thr
1865                1870                1875

Pro Met Leu Glu Asp Val Asp Glu Gly Gly Ile Arg Pro Trp His
1880                1885                1890

Leu Val Lys Pro Ser Asp Glu Pro Glu Pro Pro Arg Pro Arg Arg
1895                1900                1905

Gly Ser Leu Arg Gly Gly Glu Arg Glu Arg Ala Lys Ala Ile Pro
1910                1915                1920

Glu Ile Tyr Leu Thr Arg Leu Leu Ser Met Lys Gly Thr Leu Gln
1925                1930                1935

Lys Phe Val Asp Asp Leu Phe Gln Val Ile Leu Ser Thr Ser Arg
1940                1945                1950

Pro Val Pro Leu Ala Val Lys Tyr Phe Phe Asp Leu Leu Asp Glu
1955                1960                1965

Gln Ala Gln Gln His Gly Ile Ser Asp Gln Asp Thr Ile His Ile
1970                1975                1980
```

```
Trp Lys Thr Asn Ser Leu Pro Leu Arg Phe Trp Ile Asn Ile Ile
1985             1990                 1995

Lys Asn Pro Gln Phe Val Phe Asp Val Gln Thr Ser Asp Asn Met
2000             2005                 2010

Asp Ala Val Leu Leu Val Ile Ala Gln Thr Phe Met Asp Ala Cys
2015             2020                 2025

Thr Leu Ala Asp His Lys Leu Gly Arg Asp Ser Pro Ile Asn Lys
2030             2035                 2040

Leu Leu Tyr Ala Arg Asp Ile Pro Arg Tyr Lys Arg Met Val Glu
2045             2050                 2055

Arg Tyr Ala Asp Ile Arg Gln Thr Val Pro Ala Ser Asp Gln
2060             2065                 2070

Glu Met Asn Ser Val Leu Ala Glu Leu Ser Trp Asn Tyr Ser Gly
2075             2080                 2085

Asp Leu Gly Ala Arg Val Ala Leu His Glu Leu Tyr Lys Tyr Ile
2090             2095                 2100

Asn Lys Tyr Tyr Asp Gln Ile Ile Thr Ala Leu Glu Glu Asp Gly
2105             2110                 2115

Thr Ala Gln Lys Met Gln Leu Gly Tyr Arg Leu Gln Gln Ile Ala
2120             2125                 2130

Ala Ala Val Glu Asn Lys Val Thr Asp Leu
2135             2140

<210> SEQ ID NO 112
<211> LENGTH: 7308
<212> TYPE: DNA
<213> ORGANISM: Homo sapiens

<400> SEQUENCE: 112
gcccggccga cgcggctttg tctcctttgt tcccggcggt ggcagcgccg cgcgggaggg      60
gcgggcagcg gcgcagttt tccgcccctc ggtctccggg taacagctgc ggctccacca     120
gacccgggga gaggccgctg cgcgcggagc ccgagcccgg agcggccgac gcccgcctcg     180
gcgcgcacat cccgcggggc ccggccgggt ggtgactccc acacgggtca tgctgttgtc     240
tcctgatcca gccggccctg ccaggtgacc atgcctgctc tgggcccagc tcttctccag     300
gctctctggg ccgggtgggt cctcaccctc cagcccttc caccaactgc attcactccc      360
aatggcacgt atctgcagca cctggcaagg accccacct caggcaccct ctacctgggg      420
gctaccaact tcctgttcca gctgagccct gggctgcagc tggaggccac agtgtccacc     480
ggccctgtgc tagacagcag ggactgcctg ccacctgtga tgcctgatga gtgccccag      540 gcccagccta ccaacaaccc gaatcagctg ctcctggtga gcccagggc cctggtggta     600 tgcgggagcg tgcaccaggg ggtctgtgaa cagcggcgcc tggggcagct cgagcagctg     660
ctgctgcggc cagagcggcc tggggacaca caatatgtgg ctgccaatga tcctgcggtc     720
agcacggtgg ggctggtagc ccagggcttg gcaggggagc cctcctgtt tgtgggggga     780 ggatacacca gcaggggtgt gggggtggc attccaccca tcacaacccg ggccctgtgg     840
ccgcccgacc cccaagctgc cttctcctat gaggagacag ccaagctggc agtgggccgc     900
ctctccgagt acagccacca cttcgtgagt gcctttgcac gtggggccag cgcctacttc     960
ctgttcctgc ggcgggacct gcaggctcag tctagagctt ttcgtgccta tgtatctcga    1020
gtgtgtctcc gggaccagca ctactactcc tatgtggagt tgcctctggc tgcgaaggt    1080 ggccgctacg ggctgatcca ggctgcagct gtggccacgt ccaggaggt ggcgcatggg    1140
```

```
gaggtgctct tgcagctttt ctcctcggct gcaccccca ctgtgggccg gcccccatcg      1200
gcggctgctg gggcatctgg agcctctgcc ctctgtgcct tcccctgga tgaggtggac      1260 cggcttgcta atcgcacgcg agatgcctgc tacacccggg agggtcgtgc tgaggatggg      1320
accgaggtgg cctacatcga gtatgatgtc aattctgact gtgcacagct gccagtggac      1380
accctggatg cttatccctg tggctcagac cacacgccca gccccatggc cagccgggtc      1440
ccgctggaag ccacaccaat tctggagtgg ccagggattc agctaacagc tgtggcagtc      1500
accatggaag atggacacac catcgctttc ctgggtgata gtcaagggca gctgcacagg      1560
gtctacttgg gcccagggag cgatggccac ccatactcca cacagagcat ccagcagggg      1620
tctgcagtga gcagagacct cacctttgat gggacctttg agcacctgta tgtcatgacc      1680
cagagcacac ttctgaaggt tcctgtggct tcctgtgctc agcacctgga ctgtgcatct      1740
tgccttgctc acagggaccc atactgtggg tggtgcgtgc tccttggcag gtgcagtcgc      1800
cgttctgagt gctcgagggg ccagggccca gagcagtggc tatggagctt ccagcctgag      1860
ctgggctgtc tgcaagtggc agccatgagt cctgccaaca tcagccgaga ggagacgagg      1920
gaggttttcc tatcagtgcc agacctgcca ccctgtggc caggggagtc atattcctgc      1980
cactttgggg aacatcagag tcctgccctg ctgactggtt ctggtgtgat gtgcccctcc      2040 ccagaccct a gtgaggcccc agtgctgccg agaggagccg actacgtatc cgtgagcgtg      2100
gagctcagat ttggcgctgt tgtgatcgcc aaaacttccc tctctttcta tgactgtgtg      2160
gcggtcactg aactccgccc atctgcgcag tgccaggcct gtgtgagcag ccgctggggg      2220
tgtaactggt gtgtctggca gcacctgtgc acccacaagg cctcgtgtga tgctgggccc      2280
atggttgcaa gccatcagag cccgcttgtc tccccagacc ctcctgcaag aggtggaccc      2340
agcccctccc cacccacagc cccaaagcc ctggccaccc ctgctcctga caccctttccc      2400 gtggagcctg gggctccctc cacagccaca gcttcggaca tctcacctgg ggctagtcct      2460
tccctgctca gcccctgggg gccatgggca ggttctggct ccatatcttc ccctggctcc      2520
acagggtcgc ctctccatga ggagcctctc cctcccagcc ccaaaatgg acctggaacc      2580 gctgtccctg ccccactga cttcagaccc tcagccacac ctgaggacct cttggcctcc      2640
ccgctgtcac cgtcagaggt agcagcagtg ccccctgcag accctggccc cgaggctctt      2700
catcccacag tgcccctgga cctgccccct gccactgttc ctgccaccac tttcccaggg      2760
gccatgggct ccgtgaagcc cgccctggac tggctcacga gagaaggcgg cgagctgccc      2820
gaggcggacg agtggacggg gggtgacgca cccgccttct ccacttccac cctcctctca      2880
ggtgatggag actcagcaga gcttgagggc cctcccgccc ccctcatcct cccgtccagc      2940
ctcgactacc agtatgacac ccccgggctc tgggagctgg aagaggcgac cttgggggca      3000
agctcctgcc cctgtgtgga gagcgttcag ggctccacgt tgatgccggt ccatgtggag      3060
cgggaaatcc ggctgctagg caggaacctg cacctttttcc aggatggccc aggagacaat      3120
gagtgtgtga tggagctgga gggcctcgag gtggtggttg aggcccgggt cgagtgtgag      3180
ccacctccag ataccagtg ccatgtcacc tgccagcagc accagctcag ctatgaggct      3240
ctgcagccgg agctccgtgt ggggctgttt ctgcgtcggg ccggccgtct gcgtgtggac      3300
agtgctgagg ggctgcatgt ggtactgtat gactgttccg tgggacatgg agactgcagc      3360
cgctgccaaa ctgccatgcc ccagtatggc tgtgtgtggt gtgagggga gcgtccacgt      3420 tgtgtgaccc gggaggcctg tggtgaggct gaggctgtgg ccacccagtg cccagcgccc      3480
ctcatccact cggtggagcc actgactggg cctgtagacg gaggcacccg tgtcaccatc      3540
```

```
aggggctcca acctgggcca gcatgtgcag gatgtgctgg gcatggtcac ggtggctgga    3600
gtgccctgtg ctgtggatgc ccaggagtac gaggtctcca gcagcctcgt gtgcatcacc    3660
ggggccagtg gggaggaggt ggccggcgcc acagcggtgg aggtgccggg aagaggacgt    3720
ggtgtctcag aacacgactt tgcctaccag gatccgaagg tccattccat cttcccggcc    3780
cgcggcccca gagctggggg cacccgtctc accctgaatg ctccaagct cctgactggg     3840
cggctggagg acatccgagt ggtggttgga gaccagcctt gtcacttgct gccggagcag    3900
cagtcagaac aactgcggtg tgagaccagc ccacgcccca cgcctgccac gctccctgtg    3960
gctgtgtggt ttggggccac ggagcggagg cttcaacgcg gacagttcaa gtataccttg    4020
gaccccaaca tcacctctgc tggccccacc aagagcttcc tcagtggagg acgtgagata    4080
tgcgtccgtg ccagaatctg gacgtggta cagacgccaa gaatccgggt gaccgtggtc      4140
tcgagaatgc tgcagcccag ccaggggctt ggacggaggc gtcgcgtggt cccggagacg    4200
gcatgttccc ttggaccctc ctgcagtagc cagcaatttg aggagccgtg ccatgtcaac    4260
tcctcccagc tcatcacgtg ccgcacacct gccctcccag gctgcctga ggaccccctgg   4320
gtccgggtgg aatttatcct tgacaacctg gtctttgact ttgcaacact gaaccccaca    4380
cctttctcct atgaggccga ccccaccctg cagccactca accctgagga ccccaccatg    4440
ccattccggc acaagcctgg gagtgtgttc tccgtggagg gggagaacct ggaccttgca    4500
atgtccaagg aggaggtggt ggctatgata ggggatggcc cctgtgtggt gaagacgctg    4560
acgcggcacc acctgtactg cgagcccccc gtggagcagc ccctgccacg gcaccatgcc    4620
ctccgagagg cacctgactc tttgcctgag ttcacggtgc agatggggaa cttgcgcttc    4680
tccctgggtc acgtgcagta tgacggcgag agccctgggg cttttcctgt ggcagcccag    4740
gtgggcttgg gggtgggcac ctctcttctg gctctgggtg tcatcatcat tgtcctcatg    4800
tacaggagga agagcaagca ggccctgagg gactataaga aggttcagat ccagctggag    4860
aatctggaga gcagtgtgcg ggaccgctgc aagaaggaat tcacagacct catgactgag    4920
atgaccgatc tcaccagtga cctcctgggc agcggcatcc ccttcctcga ctacaaggtg    4980
tatgcggaga ggatcttctt ccctgggcac cgcgagtcgc ccttgcaccg ggacctgggt    5040
gtgcctgaga gcagacggcc cactgtggag caagggctgg ggcagctctc taacctgctc    5100
aacagcaagc tcttcctcac caagttcatc cacacgctgg agagccagcg caccttttca    5160
gctcgggacc gtgcctacgt ggcatctctg ctcaccgtgg cactgcatgg gaagcttgag    5220
tatttcactg acatcctccg cactctgctc agtgacctgg ttgcccagta tgtggccaag    5280
aaccccaagc tgatgctgcg caggacagag actgtggtgg agaagctgct caccaactgg    5340
atgtccatct gtctgtatac cttcgtgagg gactccgtag gggagcctct gtacatgctc    5400
tttcgaggga ttaagcacca agtggataag gggccagtgg acagtgtgac aggcaaggcc    5460
aaatacacct tgaacgacaa ccgcctgctc agagaggatg tggagtaccg tcccctgacc    5520
ttgaatgcac tattggctgt ggggcctggg gcaggagagg cccagggcgt gcccgtgaag    5580
gtcctagact gtgacaccat ctcccaggca aggagaagaa tgctggacca gctttataaa    5640
ggagtgcctc tcacccagcg gccagaccct cgcaccttg atgttgagtg gcggtctggg    5700
gtggccgggc acctcattct ttctgacgag gatgtcactt ctgaggtcca gggtctgtgg    5760
aggcgcctga acacactgca gcattacaag gtcccagatg gagcaactgt ggccctcgtc    5820
ccctgcctca ccaagcatgt gctccgggaa aaccaggatt atgtccctgg agagcggacc    5880
```

-continued

```
ccaatgctgg aggatgtaga tgagggggc atccggccct ggcacctggt gaagccaagt    5940
gatgagccgg agccgcccag gcctcggagg ggcagccttc ggggcgggga gcgtgagcgc    6000
gccaaggcca tccctgagat ctacctgacc cgcctgctgt ccatgaaggg caccctgcag    6060
aagttcgtgg atgacctgtt ccaggtgatt ctcagcacca gccgcccgt gccgctcgct    6120 gtgaagtact tctttgacct gctggatgag caggcccagc agcatggcat ctccgaccag    6180
gacaccatcc acatctggaa gaccaacagc ttgcctctga ggttctggat caatataata    6240
aaaaacccgc agtttgtgtt cgacgtgcaa acatctgata acatggatgc ggtgctcctt    6300
gtcattgcac agaccttcat ggacgcctgc accctggccg accacaagct gggccgggac    6360
tccccgatca acaaacttct gtatgcacgg gacattcccc ggtacaagcg gatggtggaa    6420
aggtactatg cagacatcag acagactgtc ccagccagcg accaagagat gaactctgtc    6480
ctggctgaac tgtcctggaa ctactccgga gacctcgggg cgcgagtggc cctgcatgaa    6540
ctctacaagt acatcaacaa gtactatgac cagatcatca ctgccctgga ggaggatggc    6600
acggcccaga agatgcagct gggctatcgg ctccagcaga ttgcagctgc tgtggaaaac    6660
aaggtcacag atctatagga acccaggagc cacggcctgc tgttgcttca gcctggcctg    6720
ggcagccctg gaagctcgga ggagaggcca ccttcttagg tgcctgtagt gactgacaag    6780
cagagttagt ggaaggtgac tcccagtctc ctggtggctc tggcctcggc cctgctggat    6840
ccacctccta gacccggggc ctcaaggctc atggggtagt acccagcctg ctccccgagt    6900
ccagcgaccc tgtgacaccg gtctgcaggg agttggggac taagggcttc cagagagtgg    6960
ctggaagaga ctccaggccc ctggggagac tgtactgttc ctgaacactg gccttggcca    7020
cactgggatt cggagaggaa ggaggagagc cccatgcttc ctgtctgcct cctccaccat    7080
ccctgacctc agttgagctg cctctggcct tgttgctgct gccacatcct aggtctaaga    7140
gttgaacgcc tctcctaggc cactacaaac tgacccctca gcagggctgg ctgccacagg    7200
gctgccctgc ctcataggta gccatggtga gggctatctg ctgcaggggg gtcttgggga    7260
gagtggtgac tccattgacc cagcttttca ttaaaggata acacactg              7308
```

CANCER ASSOCIATED PLEXIN B1 MUTATIONS

This application is the U.S. national phase of international application PCT/GB2003/005223, filed 28 Nov. 2003, which designated the U.S. and claims benefit of GB 0227908.1, filed 29 Nov. 2002, the entire contents of each of which are incorporated herein by reference.

This invention relates to the identification of cancer-associated mutations in components of the semaphorin signalling pathway, in particular in the plexinB1 transmembrane receptor.

Semaphorins were first identified as extra-cellular cues for axon guidance in the nervous system and have since been shown to have roles in cell-cell communication and cell migration in a variety of adult and embryonic tissues (Kolodkin, A. L. et al. Cell 75 7 (1993): 1389-99; Kolodkin, A. L. Prog. Brain Res. 117 (1998): 115-32; Zou, Y. et al. Cell 102 3 (2000): 363-75).

Semaphorin signalling is mediated by transmembrane receptors called plexins, which can be grouped into 4 sub-families, plexin-A, B, C and D (Tamagnone, L. and P. M. Comoglio. Trends Cell Biol. 10 9 (2000): 377-83: Tamagnone, L. et al. Cell 99 1 (1999): 71-80: WO01/14420).

PlexinB1 has been shown to interact with a variety of factors, including semaphorin 4D, c-Met, neuropilins, active Rac1 and the guanine nucleotide exchange factors (GEFS), PDZ-RhoGEF and LARG (Kolodkin, A. L. et al. Cell 90.4 (1997): 753-62; Hirotani, M. et al. Biochem. Biophys. Res. Commun. 297.1 (2002): 32-37; Vikis, H. G. et al. Proc. Natl. Acad. Sci. U.S.A 97 23 (2000) 12457-62; Driessens, M. H. et al. Curr. Biol. 11.5 (2001) 339-44; Driessens, M. et al. FEBS Lett. 529.2-3 (2002) 168; Aurandt, J. et al. Proc. Natl. Acad. Sci. U.S.A 99 19 (2002) 12085-90; Perrot, V. et al J. Biol. Chem. 277.45 (2002) 43115-20; Swiercz, J. M. et al. Neuron 35.1 (2002): 51-63). Despite these interactions, the exact function of plexinB1 is not yet known.

The present inventors have now identified mutations in plexinB1 that are closely associated with cancer. The frequency of these mutations, in particular in prostate and breast cancer, indicates that they may be useful in screening and diagnosis of cancer and as drug targets in the development of anti-cancer therapeutics.

One aspect of the invention provides a method of assessing an individual for a cancer condition comprising;
  providing a tissue sample obtained from said individual, and;
  determining the presence in said sample of one or more cells comprising a plexinB1 nucleic acid sequence having one or more mutations therein.

The presence of one or more cells comprising a mutant plexinB1 nucleic acid sequence in a sample obtained from an individual may be indicative of said individual having or being at risk of having a cancer condition. The one or more mutations in the nucleic acid sequence may alter the expression and/or activity of the encoded plexinB1 polypeptide.

A cancer condition as described herein may include any type of solid cancer and malignant lymphoma and especially leukaemia, sarcomas, skin cancer, bladder cancer, breast cancer, uterus cancer, ovary cancer, prostate cancer, lung cancer, colorectal cancer, cervical cancer, liver cancer, head and neck cancer, oesophageal cancer, pancreas cancer, renal cancer, stomach cancer and cerebral cancer. In particular, methods of the invention may be useful in the treatment of breast or prostate cancer.

An individual may be healthy or may be suspected of or at risk of suffering from a cancer condition. In other embodiments, an individual may be suffering from a cancer condition. In some embodiments, an individual may be undergoing a cancer treatment and methods of the invention may be useful in determining the progress of the treatment.

A sample obtained from an individual may be a tissue sample comprising one or more cells, for example a biopsy from a cancerous tissue as described above, or, in certain contexts, a non-cancerous tissue.

Methods of the invention may be useful in characterising a cancer condition, for example for prognostic purposes. For example, the presence of a plexinB1 nucleic acid or polypeptide having one or more mutations as described herein may indicate that the cancer condition is an invasive or metastatic cancer condition e.g. a cancer condition which is prone to or has a high probability of metastasis. In some embodiments, a method may comprise determining the level or amount of cells having a plexinB1 mutation in sample, for example a sample from a primary tumour. An increased level of cells in the sample comprising a mutant plexinB1 sequence may be indicative that the cancer condition is invasive or susceptible to metastasis.

A mutant plexinB1 nucleic acid may comprise a nucleotide sequence which has one or more mutations relative to the wild-type plexinB1 nucleotide sequence, as set out in AB007867. The mutations may be deletions, insertions or substitutions of one or more nucleotides. The one or more mutations may be in a coding or non-coding region of the plexin nucleic acid sequence and may alter the expression or function of the plexinB1 polypeptide. In other words, the mutant nucleic acid may encode a mutant plexinB1 polypeptide sequence with aberrant activity, or may encode a wild-type plexinB1 polypeptide which is expressed at an aberrant e.g. an increased or reduced, level, for example by means of an alteration in the activity of a plexinB1 regulatory element. A mutant nucleic acid may have one, two, three, four or more mutations relative to the wild-type sequence.

In some embodiments, the one or more mutations may occur in the region of the nucleic acid which encodes the cytoplasmic domain of the plexinB1 polypeptide, for example in the nucleotide sequence corresponding to exons 22, 23, 24, 25, 26, 27, 28 or 29. In some embodiments, a mutation may be in the Rac1 binding region (i.e. amino acid residues 1724-1870: Driessens et al (2001) Curr Biol 11 339-344). Such a nucleic acid sequence may have a mutation at one or more mutation positions selected from the group consisting of 5059, 5060, 5074, 5107, 5359, 5401, 5452, 5458, 5468, 5474, 5596, 5653, 5662, 5674, 5713, 5714 and 5980 relative to the wild-type plexinB1 coding sequence. The mutation may be selected from the group consisting of C5059T, C5060T, G5074A, A5107G, A5359G, T5401A, G5452A, G5458A, T5468C, A5474G, A5596G, A5653G, C5662T, A5674G, C5713T, T5714C and C5980T.

The nucleic acid sequence may be a genomic sequence, for example a genomic sequence comprising one or more of exons 22, 23, 24, 25, 26, 27, 28 and 29, or may be an RNA or cDNA sequence.

As described above, a mutant plexin nucleic acid sequence may encode a plexinB1 polypeptide having one or more mutations therein. A method of assessing an individual for a cancer condition according to the invention may thus comprise; providing a tissue sample obtained from the individual, and; determining the presence in the sample of one or more cells comprising a mutant plexinB1 polypeptide. The presence of one or more such cells may be indicative of said individual having or being at risk of having a cancer condition.

A mutant plexinB1 polypeptide may comprise an amino acid sequence which has one or more mutations relative to the wild-type plexinB1 sequence set out in AB007867. The mutations may be deletions, insertions or substitutions of one or more amino acids. In some embodiments, the mutations may occur in the cytoplasmic domain of the plexinB1 polypeptide. A mutant polypeptide may have one, two, three, four or more mutations relative to the wild-type sequence.

The one or more mutations may, for example, occur at a mutation site in the plexinB1 amino acid sequence selected from the group consisting of K1613, T1697, G1728, A1730, T1733, T1776, T1795, T1802, P1597, P1798, F1711, G1602, L1815, N1735 and R1904. Suitable mutations include substitutions selected from the group consisting of T1697A, G1728S, A1730, T17331, T1776A, T1795A, T1802A, P1597L, P1597S, P1798S, F17111, G1602T, L1815P, L1815F, K1613E, N1735S and R1904W.

Amino acid residues in the plexinB1 sequence are numbered herein in a N to C direction, starting at the initiating Met residue, which is numbered 1, as set out in AB007867.1

The presence of the one or more cells in the test sample may be determined by detecting the presence of a nucleic acid sequence encoding the mutant plexinB1 polypeptide or by detecting the presence of the mutant plexinB1 polypeptide.

Various methods are available for determining the presence or absence in a test sample of a particular nucleic acid sequence, for example a nucleic acid sequence which has a particular nucleotide at a site of mutation. Furthermore, having sequenced nucleic acid of an individual or sample, the sequence information can be retained and subsequently searched without recourse to the original nucleic acid itself. Thus, for example scanning a database of sequence information using computer or other electronic technology may identify a sequence alteration or mutation.

Methods according to some aspects of the present invention may comprise determining the binding of an oligonucleotide probe to nucleic acid obtained from the sample, for example, genomic DNA, RNA or cDNA. The probe may comprise a nucleotide sequence which binds specifically to a nucleic acid in the presence of one or more mutations and does not bind specifically to the nucleic acid in the absence of the one or more mutations or vice versa.

The oligonucleotide probe may comprise a label and binding of the probe may be determined by detecting the presence of the label.

A method may include hybridisation of one or more (e.g. two) oligonucleotide probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined.

Nucleic acid may be screened using a variant- or allele-specific probe. Such a probe may correspond in sequence to a region of the plexinB1 gene, or its complement, which contains one or more of the mutations described herein, which are shown to be associated with cancer. Under suitably stringent conditions, specific hybridisation of such a probe to nucleic acid from a sample is indicative of the presence of the mutation in the test nucleic acid. For efficient screening purposes, more than one probe may be used on the same test sample.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridisation overnight at 42° C. in 6×SSC and washing in 6×SSC at a series of increasing temperatures from 42° C. to 65° C.

Other suitable conditions and protocols are described in Molecular Cloning: a Laboratory Manual: 3rd edition, Sambrook & Russell, 2001, Cold Spring Harbor Laboratory Press NY and Current Protocols in Molecular Biology, Ausubel et al. eds. John Wiley & Sons, 1992.

Nucleic acid, which may be genomic DNA, RNA or cDNA, or an amplified region thereof, may be sequenced to identify or determine the presence of a mutation therein. A mutation may be identified by comparing the sequence obtained with the nucleotide sequence of AB007867 (SEQ ID NOs: 111 and 112). A mutation may be a deletion, substitution or insertion of one or more nucleotides relative to the AB007867 sequence (SEQ ID NOs: 111 and 112). In particular, the presence of one or more mutations identified herein to be associated with cancer may be determined.

Sequencing may be performed using any one of a range of standard techniques. Sequencing of an amplified product may, for example, involve precipitation with isopropanol, resuspension and sequencing using a TaqFS+Dye terminator sequencing kit. Extension products may be electrophoresed on an ABI 377 DNA sequencer and data analysed using Sequence Navigator software.

Since it will not generally be time- or labour-efficient to sequence all nucleic acid in a sample or even the whole PlexinB1 gene or coding sequence, a specific amplification reaction such as PCR using one or more pairs of primers may conveniently be employed to amplify the region of interest within the nucleic acid sequence, for example, the portion of the sequence suspected of containing cancer associated mutations. The amplified nucleic acid may then be sequenced as above, and/or tested in any other way to determine the presence or absence of a particular feature.

Suitable amplification reactions include the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)). PCR comprises steps of denaturation of template nucleic acid (if double-stranded), annealing of primer to target, and polymerisation. The nucleic acid used as template in the amplification reaction may be genomic DNA.

Other specific nucleic acid amplification techniques include strand displacement activation, the Qβ replicase system, the repair chain reaction, the ligase chain reaction, rolling circle amplification and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic amplification reaction available in the art.

Methods of the present invention may therefore comprise amplifying a portion of the plexinB1 coding sequence containing one or more sites of mutation from one or more cells from said tissue sample.

Mutation- or variant-specific oligonucleotides may be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the polymorphism on a denaturing polyacrylamide DNA sequencing gel, with specific bands that are linked to the gene variants being selected.

An oligonucleotide for use in nucleic acid amplification may be about 30 or fewer nucleotides in length (e.g. 18, 21 or 24). Generally specific primers are upwards of 14 nucleotides in length, but need not be more than 18-20.

In some embodiments, the region of nucleic acid sample comprising a position of mutation may be amplified using a pair of oligonucleotide primers, of which the first member of the pair comprises a nucleotide sequence which hybridises to a complementary sequence which is proximal to and 5' of the position of mutation, and the second member of the primer pair comprises a nucleotide sequence which hybridises to a complementary sequence which is proximal to and 3' of the position of mutation.

Mutation sites within the plexin B1 nucleotide sequence are discussed elsewhere herein.

In other embodiments, the first member of the pair of oligonucleotide primers may comprise a nucleotide sequence which hybridises to a complementary sequence which is proximal to and 5' or 3' of the mutation site, and the second member of the pair may comprise a nucleotide sequence which hybridises under stringent conditions to a sequence which includes a particular nucleotide (i.e. A, G, T or C) at the mutation site and not to sequences which include other nucleotides at the mutation site, such that amplification only occurs in the presence of the particular nucleotide at the mutation site.

Another aspect of the invention provides a pair of oligonucleotide amplification primers suitable for use in the methods described herein.

A suitable pair of amplification primers according to this aspect may have a first member comprising a nucleotide sequence which hybridises to a complementary sequence which is proximal to and 5' of a mutation site in the plexinB1 coding sequence, for example a mutation site in the sequence encoding the cytoplasmic domain of the polypeptide, such as at position 5059, 5060, 5074, 5107, 5359, 5401, 5452, 5458, 5468, 5474, 5596, 5653, 5662, 5674, 5713, 5714 or 5980, and; a second member comprising a nucleotide sequence which hybridises to a complementary sequence which is proximal to and 3' of the mutation site.

The first member may hybridise to a first nucleic acid strand having a sequence as shown in AB007867, and the second member may hybridise to a strand complementary to the first strand.

The identity of the nucleotide at the position of mutation may then be determined by determining the binding of an oligonucleotide probe to the amplified region. A suitable oligonucleotide probe comprises a nucleotide sequence that binds specifically to a sequence comprising a particular nucleotide at the mutation site and does not bind specifically to other sequences comprising other residues at the mutation site.

Other suitable pairs of amplification primers may have a first member comprising a nucleotide sequence which hybridises to a complementary sequence which is proximal to and 5' or 3' of a mutation site, for example a mutation site in the sequence encoding the cytoplasmic domain of the polypeptide, such as at position 5059, 5060, 5074, 5107, 5359, 5401, 5458, 5452, 5468, 5474, 5596, 5653, 5662, 5674, 5713, 5714 or 5980 of the plexinB1 coding sequence, and a second member of the pair comprising a nucleotide sequence which hybridises under stringent conditions to a sequence comprising a particular nucleotide at the mutation site and not to sequences having other nucleotides at the mutation site, such that amplification only occurs in the presence of the particular nucleotide.

An alternative or supplement to looking for the presence of mutant sequences in a test sample is to look for the presence of the normal, wild type sequence, e.g. using a suitably specific oligonucleotide probe or primer. Use of oligonucleotide probes and primers has been discussed in more detail above.

A further aspect of the present invention provides an oligonucleotide which hybridises specifically to a nucleic acid sequence which comprises a particular nucleotide at a mutation site within the plexinB1 nucleic acid sequence, for example within the coding sequence at a position selected from the group consisting of 5059, 5060, 5074, 5107, 5359, 5401, 5452, 5458, 5468, 5474, 5596, 5653, 5662, 5674, 5713, 5714 and 5980.

Such oligonucleotides may be used in a method of screening nucleic acid. Some preferred oligonucleotides have a sequence which is complementary to the plexinB1 coding sequence, or a sequence which differs from such a sequence by addition, substitution, insertion or deletion of one or more nucleotides, but preferably without abolition of ability to hybridise selectively to a sequence comprising a particular residue (i.e. one of A, G, C or T) at a mutation site as described herein, that is wherein the degree of similarity of the oligonucleotide or polynucleotide with one of the sequences given is sufficiently high.

In some preferred embodiments, oligonucleotides according to the present invention are at least about 10 nucleotides in length, more preferably at least about 15 nucleotides in length, more preferably at least about 20 nucleotides in length. Oligonucleotides may be up to about 100 nucleotides in length, more preferably up to about 50 nucleotides in length, more preferably up to about 30 nucleotides in length.

Approaches that rely on hybridisation between a probe and test nucleic acid and subsequent detection of a mismatch may be employed. Under appropriate conditions (temperature, pH etc.), an oligonucleotide probe will hybridise with a sequence that is not entirely complementary. The degree of base pairing between the two molecules will be sufficient for them to anneal despite a mis-match. Various approaches are well known in the art for detecting the presence of a mis-match between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full-length probe/test hybrid.

Thus, an oligonucleotide probe that has the sequence of a region of the normal plexinB1 coding sequence (either sense or anti-sense strand) in which the mutations associated with cancer or cancer susceptibility as described herein are known to occur, (e.g. the sequence encoding the cytoplasmic domain) may be annealed to test nucleic acid and the presence or absence of a mis-match determined.

Detection of the presence of a mis-match may indicate the presence in the test nucleic acid of a mutation associated with cancer or cancer susceptibility. On the other hand, an oligonucleotide probe that has the sequence of a region of the gene including a mutation associated with cancer or cancer susceptibility may be annealed to test nucleic acid and the presence or absence of a mis-match determined. The presence of a mis-match may indicate that the nucleic acid in the test sample has the normal sequence (the absence of a mis-match indicating that the test nucleic acid has the mutation). In either case, a battery of probes to different regions of the gene may be employed.

Oligonucleotide probes and primers based on the sequence of plexinB1 may be designed by the ordinary skilled person using conventional primer design software. Those skilled in the art are well versed in the design of suitable primers for use processes such as PCR. Various techniques for synthesizing oligonucleotide primers are well known in the art, including phosphotriester and phosphodiester synthesis methods.

Hybridisation with allele specific oligonucleotides may be conveniently carried out using an oligonucleotide array, preferably a microarray, to determine the identity of a nucleotide present at one or more positions of mutation.

Microarrays are particularly suitable for the detection of polymorphisms (Yershov, G. et. al. (1996) PNAS USA, Genetics, Vol. 93, 4913-4918; Schena, M., 1999, DNA Microarrays "a practical approach", ISBN, 0-19-963777-6, Oxford press, editor B. D. Hames; Cheung, V. G., et. al., 1999, Nat. Genet., vol. 21, 15-19, WO84/01031, WO88/1058, WO89/01157, WO93/8472, WO95/18376/WO95/18377, WO95/24649 and EP-A-0373203).

In brief, the DNA microarray may be generated using oligonucleotides that have been selected to hybridise with the specific target mutation or polymorphism. These oligonucleotides may be applied by a robot onto a predetermined location of a glass slide, e.g. at predetermined X, Y cartesian coordinates, and immobilised. An amplified genomic product (e.g. fluorescently labelled DNA) is introduced on to the DNA microarray and a hybridisation reaction conducted so that sample RNA or DNA binds to complementary oligonucleotide sequences in a sequence-specific manner, and unbound material is washed away. Amplified sample DNA containing a mutation can thus be detected by its binding to complementary oligonucleotides on the array to produce a signal. The absence of a signal for a specific oligonucleotide probe indicates that the amplified sample does not have the corresponding mutation. The signal produced at each coordinate on the microarray is conveniently read using an automated detector in order to correlate each signal with a particular oligonucleotide.

Nucleic acid, such as an oligonucleotide probe and/or pair of amplification primers, may be provided as part of a kit for performing a method according to the invention, e.g. in a suitable container such as a vial in which the contents are protected from the external environment. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled. A kit for use in determining the presence or absence of nucleic acid of interest may include one or more articles and/or reagents for performance of the method, such as means for providing or preparing the test sample itself.

Another aspect of the present invention provides a method for determining the presence or absence of a specific nucleotide at a mutation site in the plexinB1 nucleic acid sequence in a test sample comprising:
contacting a plexinB1 nucleic acid sequence with a probe which specifically binds to a mutant plexinB1 nucleotide sequence, for example a nucleotide sequence having a particular residue at a mutation site (i.e. a mutant plexinB1 sequence), such as a sequence encoding a mutant plexinB1 polypeptide as described herein; and,
determining binding of the nucleic acid sequence and the probe.

The nucleic acid sequence may comprise one or more mutation sites selected from the group consisting of 5059, 5060, 5074, 5107, 5359, 5401, 5452, 5458, 5468, 5474, 5596, 5653, 5662, 5674, 5713, 5714 and 5980 of the plexinB1 coding sequence. The identity of the nucleotide at the one or more sites of mutation determines the sequence of the mutant plexinB1 nucleic acid and the binding of the probe.

A method for determining the presence or absence in a test sample of a mutation within a test plexinB1 nucleic acid sequence may comprise:
determining the identity of the nucleotide at one or more positions of mutation in the test sequence,
the presence of a mutation in the test plexinB1 sequence being inferred by the identity of the nucleotide at the one or more positions of mutation.

The nucleotide at the one or more positions of mutation in the test sequence may be compared with the nucleotide at the corresponding one or more positions of mutation in the wild type plexinB1 sequence. The presence of a different nucleotide in the test sequence compared to the wild type sequence at the one or more positions is indicative of the presence of a mutation.

A suitable position of mutation may include a position selected from the group consisting of positions 5059, 5060, 5074, 5107, 5359, 5401, 5452, 5458, 5468, 5474, 5596, 5653, 5662, 5674, 5713, 5714 and 5980 of the plexinB1 coding sequence.

A mutation may be a cancer-associated mutation as described herein.

The test sample may be a sample of genomic DNA, cDNA or RNA from a tissue sample obtained from an individual, for example a tumour or other tissue biopsy or a sample of biological fluid, such as a blood sample. The individual may be healthy or may be suffering from a cancer or other condition as described herein.

Optionally, such a method may comprise amplifying the plexinB1 nucleic acid sequence using a pair of oligonucleotide primers. As noted, physical detection may be employed using for example hybridisation of a suitable probe, or a transcription factor or other agent that binds nucleic acid in a sequence-specific fashion, or detection may be performed in silico using suitable data analysis techniques, e.g. on a computer.

The identity of the nucleotide at a site of mutation may be determined using a method described herein, in particular, the presence of the nucleotide other than the nucleotide in the corresponding wild-type sequence may be determined.

Mutations associated with cancer may also be detected at the protein level by detecting the presence of a mutant plexinB1 polypeptide. For practical purposes, or at least commercial purposes bearing in mind cost and time, assessment of target protein expression at the protein level may be preferred over assessment at the nucleic acid level.

A method of determining the presence, absence or level of cancer cells in a sample from an individual, may include contacting a sample with a specific binding member directed against a mutant plexiB1 polypeptide, and determining binding of the specific binding member to the sample. Binding of the specific binding member to the sample may be indicative of the presence of a cancer cell within the sample.

Preferred specific binding molecules for use in aspects of the present invention include antibodies and fragments or derivatives thereof ('antibody molecules'). Antibody molecules are described in more detail below.

A cancer cell may be a cell from any type of cancer, for example as described above. In some preferred embodiments, the cancer cell may be a prostate cancer cell or a breast cancer cell.

A mutant plexinB1 polypeptide may comprise one or more mutations, for example one, two, three or more mutations, relative to the wild-type sequence. In some embodiments, the one or more mutations may occur within the cytoplasmic domain of the polypeptide. Suitable mutations may occur at mutation sites T1697, G1728, A1730, K1613, T1733, T1776, T1795, T1802, P1597, P1798, F1711, G1602, L1815, N1735 and R1904 in the plexinB1 amino acid sequence and may, for example, include one or more substitutions selected from the group consisting of T1697A, G1728S, A1730T, K1613E, I17331, T1776A, T1795A, T1802A, P1597L, P1597S, P1798S, F17111, G1602T, L1815F, L1815P, N1735S and R1904W.

In particular, mutations in plexinB1 nucleic acid and polypeptide sequences are associated with invasive cancers which are prone to metastasise and methods of the invention may be used to determine the presence of invasive cancer cells in a sample obtained from an individual.

Another aspect of the present invention provides for a method of categorising a tissue as (i) normal, (ii) potentially or actually pre-cancerous or cancerous, dysplastic, or neoplastic or (iii) cancerous and prone to metastasise, the method including determining binding to a sample of the tissue of a specific binding member directed against a mutant plexinB1 polypeptide. The pattern or degree of binding may be compared with that for a known normal sample and/or a known abnormal sample.

A method of the invention may be used to characterise a cell, for example a cancer cell, as invasive or non-invasive, for example in the prognosis of a cancer condition. Thus, binding of (e.g.) an anti-mutant plexinB1 specific binding member to a sample provides for categorising the tissue from which the sample is derived as potentially or actually pre-cancerous or cancerous, dysplastic or neoplastic or cancerous and potentially metastatic. The method may be used to pre-screen samples before further analysis. The method may also be useful for screening or analysis of samples previously tested using another technique.

A specific binding molecule, for example an antibody molecule, may be provided in a kit, which may include instructions for use in accordance with a method of the invention. Such kits are provided as a further aspect of the invention. One or more other reagents may be included, such as labelling molecules, and so on (see below). Reagents may be provided within containers, which protect them from the external environment, such as a sealed vial. A kit may include one or more articles for providing or preparing the test sample itself, depending on the tissue of interest. A kit may include any combination of, or all of, a blocking agent to decrease non-specific staining, a storage buffer for preserving binding molecule activity during storage, staining buffer and/or washing buffer to be used during antibody staining, a positive control, a negative control and so on. Positive and negative controls may be used to validate the activity and correct usage of reagents employed in accordance with the invention and which may be provided in a kit. Controls may include samples, such as tissue sections, cells fixed on coverslips and so on, known to be either positive or negative for the presence of the mutant plexinB1. The design and use of controls is standard and well within the routine capabilities of those of ordinary skill in the art.

Samples to be subjected to a contact with a binding member in accordance with methods of the invention may be prepared using any available technique which allows binding of a specific binding molecule to the mutant plexinB1 polypeptide. Various techniques are standard in the art.

The reactivities of a binding member such as an antibody on normal and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule.

One favoured mode is by covalent linkage of each binding member with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes that catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples are horseradish peroxidase and chemiluminescence.

The mode of determining binding is not a feature of the present invention and those skilled in the art are able to choose a suitable mode according to their preference and general knowledge.

Methods of assessing a cancer condition as described herein may be employed before, during and/or after a course of cancer treatment in order to determine the progress and/or effectiveness of the treatment.

A further aspect of the invention provides an antibody molecule that binds specifically to mutant plexinB1 polypeptide. Such an antibody binds preferentially to mutant plexinB1 polypeptide relative to wild-type plexinB1 polypeptide.

Antibody molecules may be useful both in the diagnosis and therapy of cancer, in accordance with the invention.

Antibodies that are specific for a mutant plexinB1 polypeptide may be obtained using techniques that are standard in the art. Methods of producing antibodies include immunising a mammal (e.g. mouse, rat, rabbit, horse, goat, sheep, monkey or bird such as chicken) with the mutant protein or a fragment thereof, or a cell or virus that expresses the protein or fragment.

Antibodies may be obtained from immunised animals using any of a variety of techniques known in the art, and screened, preferably using binding of antibody to mutant plexinB1, or fragments comprising the cytoplasmic domain thereof. For instance, Western blotting techniques or immunoprecipitation may be used (Armitage et al, 1992, Nature 357: 80-82).

The production of specific monoclonal antibodies is also well established in the art.

As an alternative or supplement to immunising a mammal with a peptide, an antibody specific for a target may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with the target or may be one constructed using sequences obtained from an organism which has been exposed to the antigen of interest (or a fragment thereof).

An antibody molecule which is specific for a mutant plexinB1 may be conjugated or bound to a cytotoxic agent. Binding of the antibody molecule to the mutant plexinB1 may be used to selectively target the cytotoxic agent to a cancer cell. Many suitable cytotoxic agents are known in the art.

Another aspect of the invention provides a method of identifying and/or obtaining an antibody specific for a mutant plexinB1, the method comprising;

providing a population of antibody molecules specific for mutant plexinB1, contacting said population with a normal plexinB1 polypeptide, identifying one or more members of said population which bind preferentially to mutant plexinB1 relative to normal plexinB1

A method may include isolating and/or purifying said one or more members. A population of antibody molecules specific for mutant plexinB1 may be obtained as described above.

Antibodies may be modified in a number of ways. Indeed, unless context precludes otherwise, the term "antibody" should be construed as covering any specific binding substance having an antibody antigen-binding domain. Thus, this covers antibody fragments, derivatives, and functional equivalents, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

Recombinant expression of polypeptides, including antibody molecules, is well-known in the art.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is E. coli. The preferred hosts for baculovirus expression are insect cells such as the SF9 cell line.

Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 3rd edition, Sambrook & Russell 2001, Cold Spring Harbor Laboratory Press. Transformation procedures suitable for different hosts are well known in the art.

Following production by expression from encoding nucleic acid an antibody or other specific binding molecule directed against mutant or wild-type plexinB1, may be recovered and may be isolated, if necessary conjugated to an appropriate label or reporter, and provided for use in assessing a cancer condition in an individual as described herein.

Determination of binding to mutant plexinB1 polypeptide in vivo may be used to identify localisations of cancer cells in the body. Labelled binding molecules against mutant plexinB1 may be administered to an individual and binding within the body determined. When a radionucleotide such as Iodine-125, Indium-111, Thallium-201 or Technetium-99m is attached to an antibody, and the antibody localises preferentially in tumour rather than normal tissues, the presence of radiolabel in tumour tissue can be detected and quantitated using a gamma camera or scintigraphy. Radiolabelling with technetium-99m is described in Pak et al (1992), Nucl. Med. Biol. 19; 699-677. A review of cancer imaging with anti-CEA antibodies is provided by Goldenberg D. M., Int. J. of Biol. Markers 1992, 7; 183-188. The present invention of course extends to specific binding members directed against mutant plexinB1 as disclosed, for use in any such in vivo method.

As described above, mutations in the plexinB1 nucleic acid and amino acid sequences have further been shown by the inventors to be associated with the invasiveness of a cancer cell. Thus, methods of the invention may be useful in the prognosis of an individual having a cancer condition.

Another aspect of the invention provides a method of determining the invasiveness of a cancer cell from a sample obtained from an individual, the method comprising, determining the presence or absence in said cell of a plexinB1 nucleic acid having one or more mutations therein, the presence of said plexinB1 nucleic acid being indicative that the cancer cell is invasive.

Mutant plexinB1 nucleic acid is described in detail above. In particular, a mutant plexinB1 nucleic acid from an invasive cancer cell may have two or more, or three or more mutations relative to the wild-type sequence. The cancer cell may be a prostate cancer cell or other cancer cell as described above.

In some embodiments a mutant plexinB1 nucleic acid from an invasive cancer cell may include one or more of the mutations T1795A, P1597L, P1597S and L1815P. In some preferred embodiments, a mutant plexinB1 includes the mutation T1795A.

The presence of a mutant plexinB1 nucleic acid may be determined by detecting the presence of a polypeptide sequence encoded by said mutant plexinB1 polypeptide or by directly detecting the mutant plexinB1 nucleic acid, as described above.

The results set out herein show that the proportion of cells containing plexinB1 mutations is increased in metastatic tumours compared to primary tumours.

A method of determining the invasiveness or susceptibility to metastasis of a cancer condition in an individual may comprise;

determining the presence, level or amount of cancer cells which comprise a plexinB1 nucleic acid sequence having one or more mutations therein in a sample obtained from said individual.

The presence of said cells in the sample or the presence of an elevated level of said cells relative to cells with wild-type plexinB1 may be indicative that the cancer condition is susceptible to or at risk of metastasis.

Another aspect of the invention provides a method of identifying and/or obtaining a compound as a putative anti-cancer agent, the method comprising;

contacting a plexinB1 polypeptide with a test compound, and;

determining the activity of the plexinB1 polypeptide in the presence relative to the absence of test compound.

A decrease in activity in the presence relative to the absence of test compound is indicative that the compound is a putative anti-cancer agent.

The activity of the plexinB1 polypeptide may be determined by determining the binding of said polypeptide to a ligand such as semaphorin 4D, neuropilin, c-Met, active Rac1, PDZ-RhoGEF or LARG and/or by determining the activation of Rho A or the binding of Rho A to effector proteins (e.g. ROCK).

In some embodiments, the plexinB1 polypeptide may be a mutant plexinB1 polypeptide as described above. In an optional step following the identification of a test compound which alters the activity of the mutant plexinB1 polypeptide, the effect of the test compound on wild-type plexinB1 may be determined. A method according to such embodiments may comprise contacting a wild-type plexinB1 polypeptide with the test compound, and; determining the activity of the wild-type plexinB1 polypeptide.

In some embodiments, a putative anti-cancer agent may disrupt the interaction of a mutant plexinB1 polypeptide with a wild-type polypeptide. A method of the invention may comprise the steps of;

contacting the mutant plexinB1 polypeptide with the test compound in the presence of a wild-type plexinB1, and;

determining the activity of the wild-type plexinB1 polypeptide.

A test compound which preferentially inhibits the activity of mutant plexinB1 relative to wild type plexinB1 may be particularly useful in specifically targeting cancer cells.

In other embodiments, the plexinB1 polypeptide may be a wild-type plexinB1 polypeptide. A test compound may be identified which alters the activity of both the wild-type and mutant plexinB1 polypeptide. Such a compound may be particularly useful in treating cancer when specifically targeted to a tumour site, for example using tumour-specific antibodies.

An agent identified using one or more primary screens (e.g. in a cell-free system) as having ability to modulate the activity of plexinB1 may be assessed further using one or more secondary screens. A secondary screen may involve testing for effects on growth of cancer cells in vitro, in particular anchorage independent growth, or a biological function of plexinB1 or semaphorin signalling, for example in an animal model.

Suitable biological functions which may be assessed in a secondary screen include reduction in size or number of tumours, inhibition of metastasis, or a reduction in other symptoms or effects of a cancer condition.

In some embodiments, the activity of the plexinB1 polypeptide may be determined by measuring the tumourigenicity in an animal model of cancer cells, such as NIH3T3 cells, which express the plexinB1 polypeptide. Suitable animal models include athymic nude mice. A reduction in the rate of tumour production in the presence relative to the absence of test compound may be indicative that the compound is a putative anti-cancer agent which enhances or restores the tumour suppressor activity of plexinB1.

In some embodiments, test compounds may be screened initially using a secondary screen as described above, without an initial primary screening step.

One class of putative inhibitor compounds can be derived from the plexinB1 polypeptide, in particular the mutant plexinB1 polypeptide, and/or ligands which bind to it, including semaphorin 4D, active Rac1, neuropilin, PDZ-RhoGEF and LARG. Membrane permeable peptide fragments of from 5 to 40 amino acids, for example, from 6 to 10 amino acids may be tested for their ability to disrupt such interaction or activity. In some embodiments, peptide fragments may comprise the cytoplasmic domain of plexinB1, in particular one or more mutation sites within the cytoplasmic domain, as described herein.

Peptide fragments may also be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

The inhibitory properties of a peptide fragment as described above may be increased by the addition of one of the following groups to the C terminal: chloromethyl ketone, aldehyde and boronic acid. These groups are transition state analogues for serine, cysteine and threonine proteases. The N terminus of a peptide fragment may be blocked with carbobenzyl to inhibit aminopeptidases and improve stability (Proteolytic Enzymes 2nd Ed, Edited by R. Beynon and J. Bond, Oxford University Press, 2001).

Another convenient way of producing polypeptide molecules, which may be full-length sequences or peptide fragments thereof, for use in methods of the invention, is to express nucleic acid encoding it, by use of nucleic acid in an expression system.

Antibodies which specifically bind to wild-type or mutant plexinB1 polypeptide, or regions thereof, form a further class of putative inhibitor compounds. Candidate inhibitor antibodies may be characterised and their binding regions determined to provide single chain antibodies and fragments thereof which alter (i.e. enhance or disrupt) the interactions and/or activity of plexinB1.

Techniques for obtaining antibodies are standard in the art and are described elsewhere herein.

Antibody molecules may for example be micro-injected into cells, e.g. at a tumour site, subject to radio- and/or chemotherapy (as discussed already above). Antibodies may be employed in accordance with the present invention for other therapeutic and non-therapeutic purposes, which are discussed elsewhere herein.

Other candidate inhibitor compounds may be based on modelling the 3-dimensional structure of a polypeptide or peptide fragment and using rational drug design to provide potential modulator (for example, inhibitor) compounds with particular molecular shape, size and charge characteristics.

A potential modulator compound may be a "functional analogue" of a peptide or other compound which modulates mutant plexinB1 activity. A functional analogue has the same functional activity as the peptide or other compound in question, i.e. it may alter (i.e. enhance or interfere with) the binding between mutant plexinB1 and one or more ligands. Examples of such analogues include chemical compounds which are modelled to resemble the three dimensional structure of the mutant or wild-type plexinB1 polypeptide, and in particular the arrangement of the key amino acid residues as they appear in the mutant form of plexinB1.

Mutant or wild-type plexinB1 polypeptide and binding partners may be used in methods of designing mimetics of these molecules suitable for inhibiting mutant plexinB1 activity.

Accordingly, the present invention provides a method of designing mimetics of wild-type or mutant plexinB1 polypeptide having the biological activity of modulating, e.g. enhancing or inhibiting, the activity of wild-type or mutant plexinB1 polypeptide, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the design of so-called "mimetics" which involves the study of the functional interactions of the molecules and the design of compounds which contain functional groups arranged in such a manner that they could reproduced those interactions.

The modelling and modification of a 'lead' compound to optimise its properties, including the production of mimetics, is further described below.

As described above, the activity or function of a mutant plexinB1 may be inhibited, as noted, by means of a compound that interferes in some way with the interaction of plexinB1 with other factors described herein. An alternative approach to inhibition employs regulation at the nucleic acid level to inhibit activity or function by down-regulating production of the mutant form of plexinB1.

A method of identifying and/or obtaining a compound which is a putative anti-cancer agent may comprise;

contacting a plexinB1 nucleic acid therein with a test compound, and;

determining the expression of the plexinB1 nucleic acid in the presence relative to the absence of test compound.

PlexinB1 nucleic acid sequences may be mutant plexinB1 sequences i.e. sequences having one or more mutations, or wild-type sequences. PlexinB1 nucleic acid sequences are described elsewhere herein. The plexinB1 nucleic acid may be within a cell, for example in a cancer cell line, such as a breast or prostate cancer cell line.

Expression of the nucleic acid may be determined using conventional techniques, such as Northern blotting or RT-PCR.

Anti-sense or RNAi technology may be used to inhibit the expression of a plexinB1 nucleic acid, in particular a mutant plexinB1 nucleic acid. The use of these approaches to down-regulate gene expression is now well-established in the art.

Methods of the present invention may include identifying the test compound as a putative anti-cancer agent. Methods may further include isolating, purifying, synthesising and/or manufacturing a compound identified as a putative anti-cancer agent.

Optionally, compounds identified as putative anti-cancer agents using a method described herein may be modified to optimise activity or provide other beneficial characteristics such as increased half-life or reduced side effects upon administration to an individual.

Methods of the present invention may further include formulating a compound identified as a putative anti-cancer agent into a composition, such as a medicament, pharmaceutical composition or drug, with a pharmaceutically acceptable excipient as described below.

Another aspect of the invention provides a pharmaceutical composition comprising the compound as described above and a pharmaceutically acceptable excipient. Such a composition may be administered to an individual.

A method of making a pharmaceutical composition may comprise, identifying a compound as modulator of plexinB1, for example an inhibitor of mutant plexin B1 or an enhancer of wild-type plexin B1, using a method described herein, synthesising, preparing or isolating said modulator, admixing the modulator with a pharmaceutically acceptable excipient, vehicle or carrier, and optionally other ingredients to formulate or produce said composition; and, optionally, determining the activity of mutant plexinB1 as described herein in the presence of said composition.

In other embodiments, a method of producing a pharmaceutical composition may comprise;

identifying a compound which modulates the activity of a plexinB1 polypeptide using a method described herein; and, admixing the compound identified thereby with a pharmaceutically acceptable carrier.

The formulation of compositions with pharmaceutically acceptable carriers is described further below.

Another aspect of the invention provides a method for preparing a pharmaceutical composition, for example, for the treatment of a cancer condition comprising;

i) identifying a compound which is an agonist/antagonist of a plexinB1 polypeptide ii) synthesising the identified compound, and;

iii) incorporating the compound into a pharmaceutical composition.

As described above, a plexinB1 polypeptide may be a wild-type or mutant plexinB1 polypeptide.

The identified compound may be synthesised using conventional chemical synthesis methodologies. Methods for the development and optimisation of synthetic routes are well known to a skilled person.

The compound may be modified and/or optimised as described above.

Incorporating the compound into a pharmaceutical composition may include admixing the synthesised compound with a pharmaceutically acceptable carrier or excipient.

The modification of a known pharmacologically active compound to improve its pharmaceutical properties is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. The design, synthesis and testing of modified active compounds, including mimetics, may be used to avoid randomly screening large number of molecules for a target property.

There are several steps commonly taken in modifying a compound which has a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of plexinB1, in particular mutant plexinB1 as described herein, and ligands are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the modified compound is easy to synthesise, is likely to be pharmacologically acceptable, and does not degrade in vivo, while retaining the biological activity of the lead compound. Modified compounds found by this approach can then be screened to see whether they have the target property, or to what extent they exhibit it. Further optimisation or modification can then be carried out to arrive at one or more final compounds for in vivo or clinical testing.

Those of skill in the art may vary the precise format of methods of the invention using routine skill and knowledge.

Aspects of the invention provide a compound obtained by a method as described above for use in a method of treatment and the use of such a compound in the manufacture of a medicament for use in the treatment of cancer.

Another aspect of the invention provides a method of treating a cancer condition, such as prostate cancer or breast cancer, in an individual, the method comprising inhibiting the activity of mutant plexinB1 polypeptide in one or more cells of said individual.

The activity or function of mutant plexinB1 polypeptide may be inhibited, for example, by administering an antagonist of mutant plexinB1 to said individual. A suitable antagonist may be an antibody molecule, peptide or small organic molecule, and may be obtained by a method described above.

As described above, an antagonist of mutant plexinB1 may be specific for mutant plexinB1 or may have an antagonistic effect on both wild-type and mutant plexinB1. An antagonist which acts on both wild-type and mutant plexinB1 may be specifically targeted to a tumour site using conventional techniques.

An alternative approach to inhibition employs regulation at the nucleic acid level to inhibit activity or function by down-regulating production of mutant plexinB1. The activity of mutant plexinB1 polypeptide may be inhibited by reducing or abolishing expression of plexin B1 polypeptide using anti-sense or RNAi technology.

Anti-sense oligonucleotides may be designed to hybridise to the complementary sequence of nucleic acid, pre-mRNA or mature mRNA, interfering with the production of mutant plexinB1 polypeptide so that its expression is reduced or completely or substantially completely prevented. In addition to targeting coding sequence, anti-sense techniques may be used to target control sequences of a gene, e.g. in the 5' flanking sequence, whereby the antisense oligonucleotides can interfere with expression control sequences. The construction of antisense sequences and their use is described for example in Peyman and Ulman, Chemical Reviews, 90:543-584, (1990) and Crooke, Ann. Rev. Pharmacol. Toxicol., 32:329-376, (1992).

Oligonucleotides may be generated in vitro or ex vivo for administration or anti-sense RNA may be generated in vivo within cells in which down-regulation is desired. Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14-23 nucleotides, e.g. about 15, 16 or 17.

An alternative to anti-sense is to use a copy of all or part of the target gene inserted in sense, that is the same, orientation as the target gene, to achieve reduction in expression of the target gene by co-suppression; Angell & Baulcombe (1997) The EMBO Journal 16, 12:3675-3684; and Voinnet & Baulcombe (1997) Nature 389: pg 553). Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi).

RNA interference is a two-step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

RNAi may be also be efficiently induced using chemically synthesized siRNA duplexes of the same structure with 3'-overhang ends (Zamore P D et al. Cell, 101, 25-33, (2000)). Synthetic siRNA duplexes have been shown to specifically suppress expression of endogenous and heterologeous genes in a wide range of mammalian cell lines (Elbashir S M. et al. Nature, 411, 494-498, (2001))

Another possibility is that nucleic acid is used which on transcription produces a ribozyme, able to cut nucleic acid at a specific site—thus also useful in influencing gene expression. Background references for ribozymes include Kashani- Sabet and Scanlon, 1995, Cancer Gene Therapy, 2(3): 213-223, and Mercola and Cohen, 1995, Cancer Gene Therapy, 2(1), 47-59.

Thus, an inhibitor of mutant plexinB1 activity may comprise a nucleic acid molecule comprising all or part of the mutant or wild type plexinB1 coding sequence or the complement thereof.

Such a molecule may suppress the expression of the mutant plexinB1 polypeptide and may comprise a sense or anti-sense mutant plexinB1 coding sequence or may be a mutant plexinB1 specific ribozyme, according to the type of suppression to be employed.

The type of suppression will also determine whether the molecule is double or single stranded and whether it is RNA or DNA.

A related aspect of the invention provides a method of treating a cancer condition, such as prostate cancer and breast cancer, in an individual, the method comprising increasing the activity of wild-type plexinB1 polypeptide in one or more cells of said individual.

Wildtype plexinB1 activity may be enhanced by increasing the level of plexinB1 polypeptide in the one or more cells, for example by expression from a recombinant plexinB1 coding sequence, or by administration of a plexinB1 agonist molecule.

Further aspects of the invention provide a nucleic acid encoding wild-type or mutant plexinB1 polypeptide, its complement or a fragment thereof for use in a method of treatment, for example in a method of treating cancer, for example prostate cancer and the use of nucleic acid encoding wild-type or mutant plexinB1, its complement or a fragment thereof in the manufacture of a medicament for the treatment of cancer. Such molecules may, for example, be useful in suppressing the expression of mutant plexinB1 or increasing the expression of wild-type plexin B1.

Mutations in the plexinB1 coding sequence are shown herein to be associated with anchorage-independent growth and metastasis. A method of reducing the invasiveness of a tumour in an individual may comprise inhibiting the activity of mutant plexinB1 polypeptide in one or more cells of said tumour, or enhancing the activity of wild-type plexinB1 polypeptide, as described above.

A compound may be administered in a precursor form, for conversion to an active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

Whether it is a polypeptide, peptide, nucleic acid molecule, small molecule or other pharmaceutically useful compound that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Aspects of the present invention will now be illustrated with reference to the following experimental exemplification, by way of example and not limitation. Further aspects and embodiments will be apparent to those of ordinary skill in the art. All documents mentioned in this specification are hereby incorporated herein by reference.

BRIEF DESCRIPTION OF THE DRAWINGS

FIG. 3a: C5060T (pro1597Leu): i) normal sequence (SEQ ID NO:1), ii) SSCP band (SEQ ID NO:2) and iii) direct sequence (SEQ ID NO:3) of tumour sample.

FIG. 3b: C5059 (Pro1597Ser) SSCP band (SEQ ID NO:4).

FIG. 3c: G5074A (Gly1602Thr) complementary sequence: i) normal sequence (SEQ ID NO:5), ii) SSCP band (SEQ ID NO:6) and iii) direct sequence (SEQ ID NO:5) of tumour sample.

FIG. 3d: A5359G (Thr1697Ala): i) normal sequence (SEQ ID NO:7) and ii) direct sequence (SEQ ID NO:8) of tumour sample.

FIG. 3e: T5401A (Phe1711Ile) complementary sequence: i) normal sequence (SEQ ID NO:9) and ii) SSCP band (SEQ ID NO:10).

FIG. 3f: C5468T (Thr1733Ile): i) normal sequence (SEQ ID NO:11), ii) SSCP band (SEQ ID NO:12) and iii) direct sequence (SEQ ID NO:12) of tumour sample.

FIG. 3g: A5474G (Asn1735Ser): i) normal sequence (SEQ ID NO:13) and ii) direct sequence (SEQ ID NO:14) of tumour sample.

FIG. 3h: A5596G (Thr1774Ala): i) normal sequence (SEQ ID NO:15) and ii) SSCP band (SEQ ID NO:15)

FIG. 3i: A5653G (Thr1795Ala): i) normal sequence (SEQ ID NO:16), ii) SSCP band (SEQ ID NO:17) and iii) direct sequence (SEQ ID NO:16) of tumour sample.

FIG. 3j: C5662T (Pro1798Ser): i) normal sequence (SEQ ID NO:18), ii) SSCP band (SEQ ID NO:19) and iii) direct sequence (SEQ ID NO:20) of tumour sample.

FIG. 3k: A5674G (Thr1802Ala): i) normal sequence (SEQ ID NO:21) and ii) SSCP band (SEQ ID NO:22).

FIG. 3l: T5714C (Leu1815Pro) complementary sequences: i) normal sequence (SEQ ID NO:23), ii) SSCP band (SEQ ID NO:24) and iii) direct sequence (SEQ ID NO:25) of tumour sample.

FIG. 3m: C5980T (Arg1904Trp) complementary sequences: i) normal sequence (SEQ ID NO:26), ii) SSCP band (SEQ ID NO:27) and iii) direct sequence (SEQ ID NO:27) of tumour sample.

FIG. 5 shows an alignment of plexinB1 sequences with positions of the mutations shown.

| | 1593-1605 | 1693-1701 | 1707-1715 | 1724-1738 | 1772-1779 | 1791-1805 | 1811-1819 | 1899-1908 |
|---|---|---|---|---|---|---|---|---|
| HsPLXNB1 | 28 | 37 | 44 | 50 | 60 | 69 | 80 | 89 |
| Mm plxnb1 | 32 | 37 | 44 | 50 | 62 | 73 | 80 | 89 |
| Dm plexB | 33 | 39 | 46 | 55 | 63 | 74 | 83 | 91 |
| Ce plx-2 | 34 | 40 | 47 | 56 | 64 | 75 | 84 | |
| Hs PLXNB3 | 35 | 41 | 48 | 57 | 65 | 76 | 85 | 92 |
| Hs PLXB2 | 42 | 49 | 58 | 66 | 77 | 86 | 93 | |
| Hs PLXNA2 | 36 | 43 | 59 | 67 | 78 | 87 | 110 | |
| Hs PLXNA1 | 59 | 68 | 79 | 88 | 110 | | | |
| 1597 L | 29 | | | | | | | |
| 1597 S | 30 | | | | | | | |
| 1602 T | 31 | | | | | | | |
| 1697 A | | 38 | | | | | | |
| 1711 I | | | 45 | | | | | |
| 1728 S | | | | 51 | | | | |
| 1728 T | | | | 52 | | | | |
| 1728 I | | | | 53 | | | | |
| 1728 S | | | | 54 | | | | |
| 1776 A | | | | | 61 | | | |
| 1795 A | | | | | | 70 | | |
| 1795 S | | | | | | 71 | | |
| 1795 A | | | | | | 72 | | |
| 1815 P | | | | | | | 81 | |
| 1815 F | | | | | | | 82 | |
| 1904 W | | | | | | | | 90 |

Figure 6:
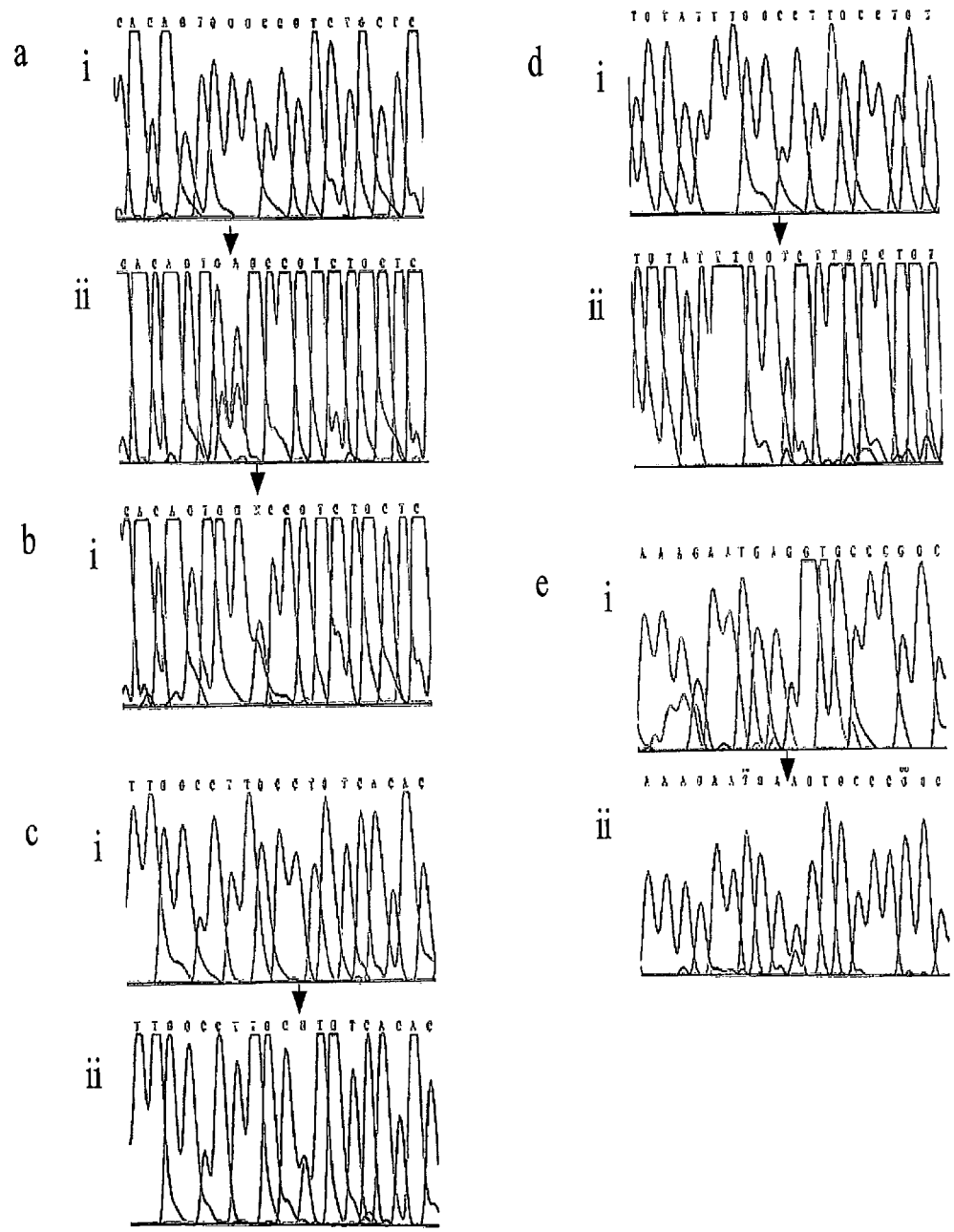

FIG. 6 shows the sequencing data for the breast cancer mutations.

FIG. 6a. T5059C (pro1597Ser) complementary sequences: i) normal sequence (SEQ ID NO:95) and ii) SSCP band (SEQ ID NO:96).

FIG. 6b. C5060T (Pro1597Leu) complementary sequence: i) SSCP band (SEQ ID NO:97).

FIG. 6c. G5424A (Gly1728Ser) complementary sequences: i) normal sequence (SEQ ID NO:98) and ii) SSCP band (SEQ ID NO:99).

FIG. 6d. G5458A (Ala1730Thr) complementary sequences: i) normal sequence (SEQ ID NO:100) and ii) SSCP band (SEQ ID NO:101).

FIG. 6e. C5713T (Leu1815Phe) complementary sequences: i) normal sequence (SEQ ID NO:102) and ii) SSCP band (SEQ ID NO:103).

Table 1 shows plexinB1 mutations in prostate cancer.
Table 2 shows plexinB1 mutations in breast cancer.

EXPERIMENTAL

Materials and Methods

Sample Preparation

Paraffin sections were cut from 95 cases of primary prostate cancer treated by radical prostatectomy and 11 metastatic cancers from patients who had relapsed following hormone treatment. Areas of cancer were identified and microdissected from the sections or obtained by laser microdissection, depending on the size of the cancer foci. PCR products were sequenced directly by cycle sequencing (4 pmole primer, Amplitaq, ABI)

In Vitro Mutagenesis

The A5359G, A5653G, and T5714C sequence changes were introduced using Quickchange kit (Stratagene) with the following primers: GTCCATCTGTCTGTATGCCTTCGT-GAGGGTGAG (SEQ ID NO:104) and CTCACCCTCAC-GAAGGCATACAGACAGATGGAC (SEQ ID NO:105), GGAGTGCCTCTCGCCCAGCGGCCAGACCCTCG (SEQ ID NO:106) and CGAGGGTCTGGCCGCTGGGC-GAGAGGCACTCC (SEQ ID NO:107), GGTGGC-CGGGCACCCCATTCTTTCTGACGAGG (SEQ ID NO:108) and CCTCGTCAGAAAGAATGGGGTGCCCG-GCCACC (SEQ ID NO:109).

The sequence change was confirmed by sequencing. No other sequence change was seen in the cytoplasmic domain.

Transfection

NIH3T3 cells were transfected with pcDNA3-PlexB1 (A5359G), pcDNA3-PlexB1(A5653G), pcDNA3-PlexB1 (T5714C), pcDNA-PlexB1 and pcDNA3 (vector only) by calcium phosphate transfection and selected with G418.

Cell Culture

LNCaP, PC3 and DU145 were grown in RPMI-1640 with 10% FCS, NIH3T3 was grown in DMEM with 10% NCS.

Anchorage Independent Assays 1000 cells were grown in 12 well plates in 0.35% agarose over a layer of 0.7% agarose in medium.

In Vivo Tumourigenesis Assays

NIH3T3 transfected with mutant, wild type or empty vector or parental NIH3T3 cells were injected subcutaneously into athymic nude mice.

Screening for Polymorphisms

Control DNA from unrelated individuals of Caucasian origin was screened for the presence of identified mutations by PCR and restriction enzyme digestion (NEB) using HaeIII (P1597L, P1597S, A1730T), AvaII (P1597S), StyI (G1602T), BstZ171 (T1697A), BclI (F1711I), BstN1 (G1728S), StyI (T17331), BsrB1 (N1735S), HgaI (T1776A), Hph1 (T1795A), HaeIII (P1798S), HhaI (T1802A), Mnl1 (L1815P, L1815F) and TaqI (R1904W). Primers with a single base pair mismatch were used for StyI, BsrB1, Mnl1 and Taq1. The T1795A mutation destroys a Hph1 site. Amplified products were digested with Hph1, Hph1-resistant DNA bands excised from the gel, sequenced and the sequence change identified.

SSCP analysis was performed as previously described (Williamson, M. P. et al Genes Chromosomes Cancer 92 (1994): 108-18).

Results

Initial RT-PCR Screen

RT-PCR of RNA from prostate cancer cell lines showed that plexins A1, A3 and B1 were expressed in prostate cells. The cDNA of the cytoplasmic domains of plexin A1, A3 and B1 was sequenced in the prostate cancer cell lines PC3, DU145, LNCaP and benign prostate cell line Pre2.8.

Figure 1:
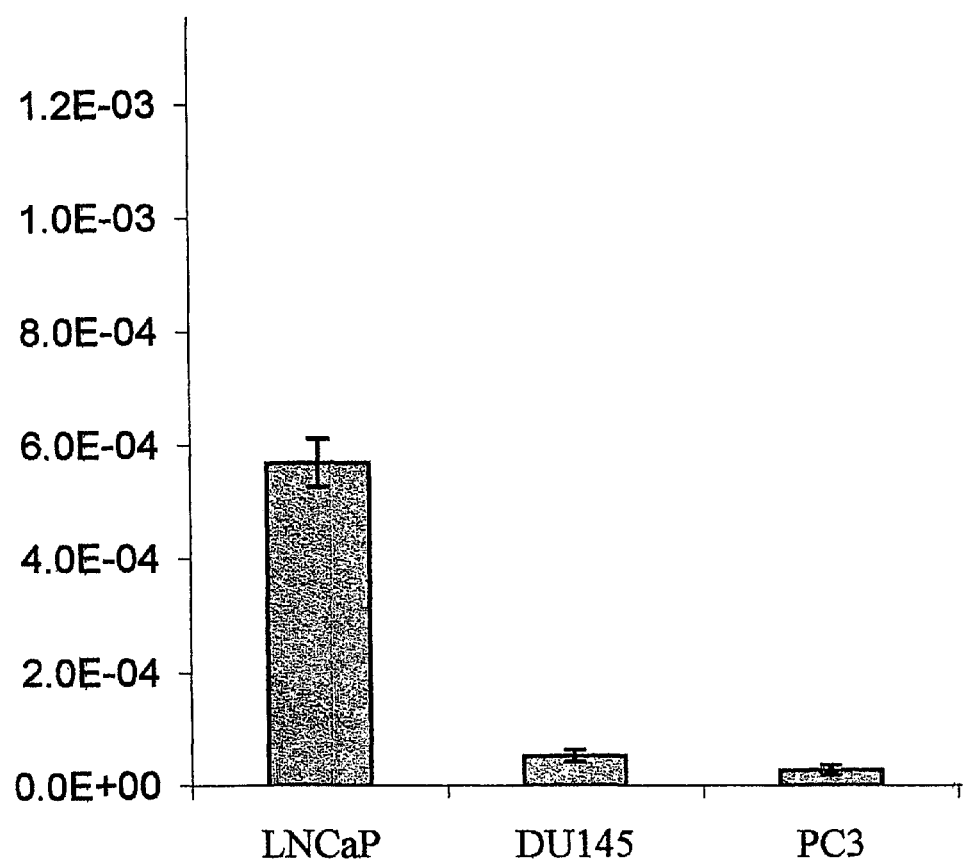
FIG. 1 shows the expression of plexinB1 in LNCaP, PC3 and DU145 cells using quantitative RT-PCR. Real time RT-PCR was performed on a Taqman 7700 using β actin template as control, average of 3 RNA extractions.
Figure 2:
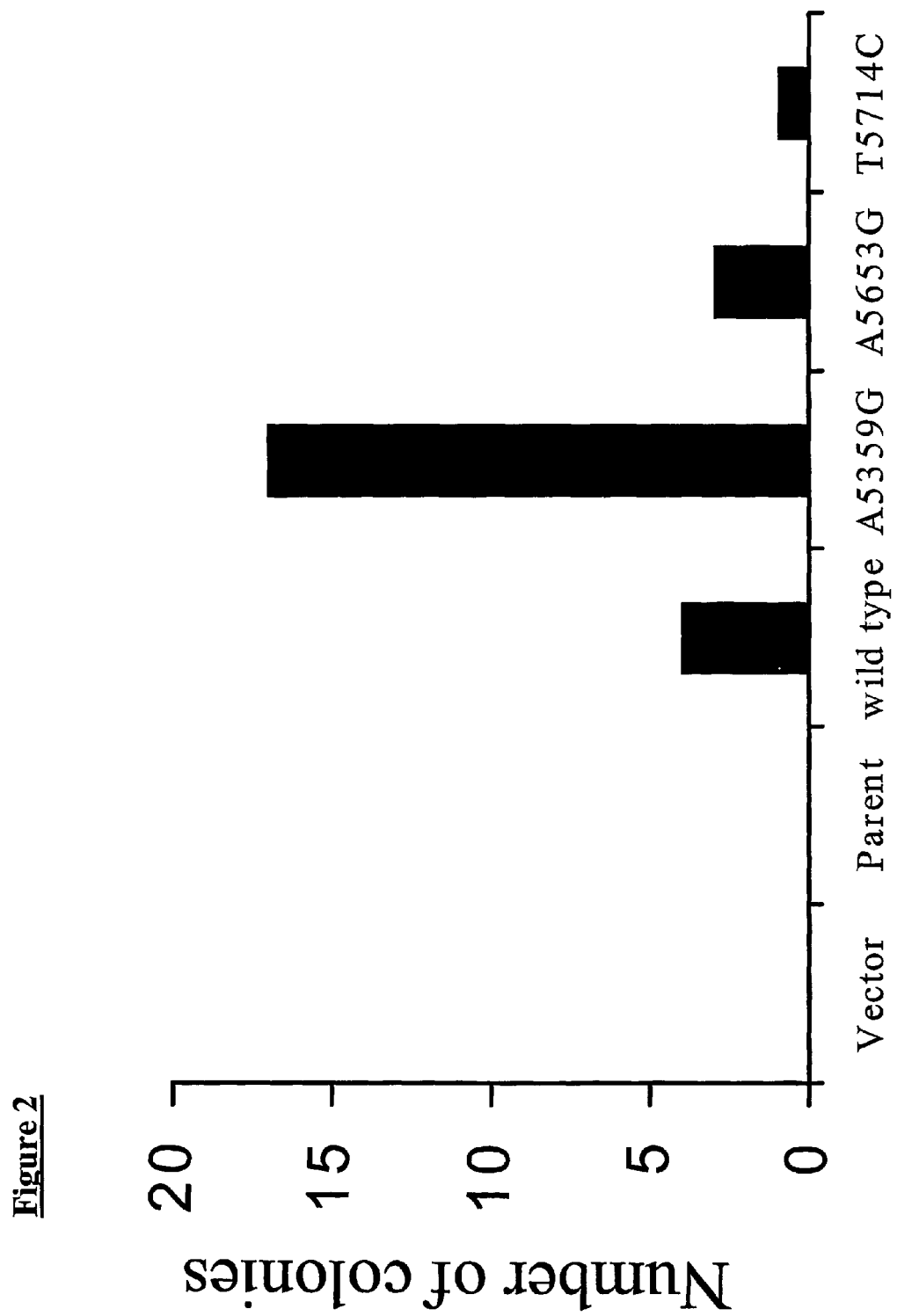
FIG. 2 shows the number of colonies of ≧200 μM produced after 3 weeks in 0.3% agarose by cells transfected with plexinB1 (A5359G), plexinB1 (A5653G), plexinB1 (T5714C), wild type plexinB1, empty vector or parental NIH3T3 cells. The bars indicate the mean number of colonies produced by 2 independent clones of each construct.

A single nucleotide change (A to G) was observed in plexin B1 in LNCaP cDNA at nucleotide 5359, which potentially changes threonine 1697 to an alanine. The sequence change is heterozygous in LNCaP cells. Karyotyping of LNCaP has revealed that this cell line has three copies of chromosome 3p. Estimation of the relative intensities of the mutant and wild type bands indicated that the mutation was present in two of the three copies of chromosome 3p. PlexinB1 is overexpressed in LNCaP as shown by quantitative RT-PCR (FIG. 1).

The sequence change was absent from 120 control chromosomes of similar genetic background to LNCaP.

DNA from 25 prostate tumours was extracted from paraffin sections and sequenced directly for the mutation found in LNCaP. The Thr1697Ala mutation was found in three of the cancers, but was absent from seminal vesicle or lymph node tissue extracted from the same patient in the two cases where such tissue was available. This sequence change therefore represents a somatic change associated with prostate cancer.

Figure 3:
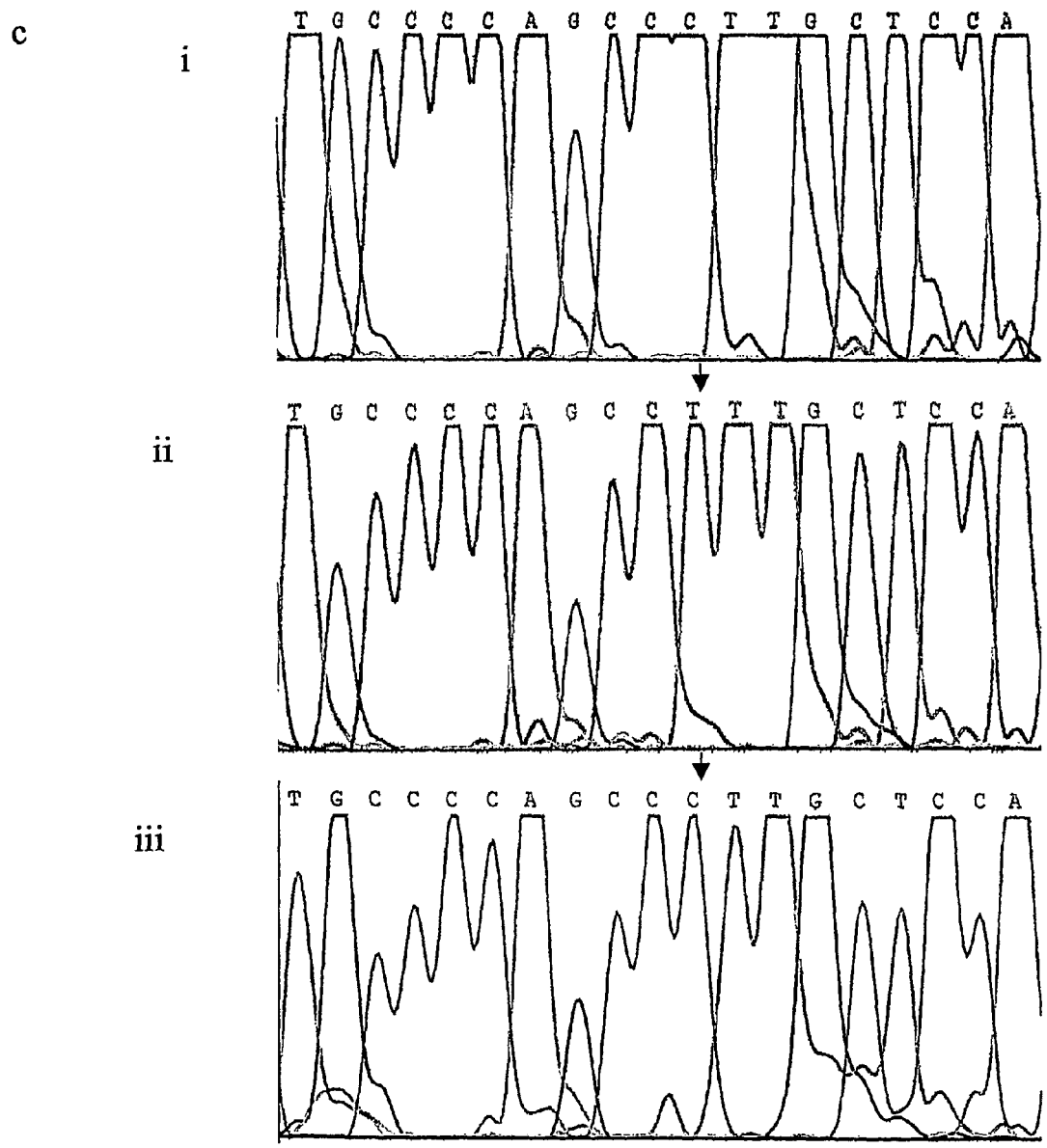
FIG. 3 shows sequencing data for plexin B1 prostate cancer mutations.
Figure 3:
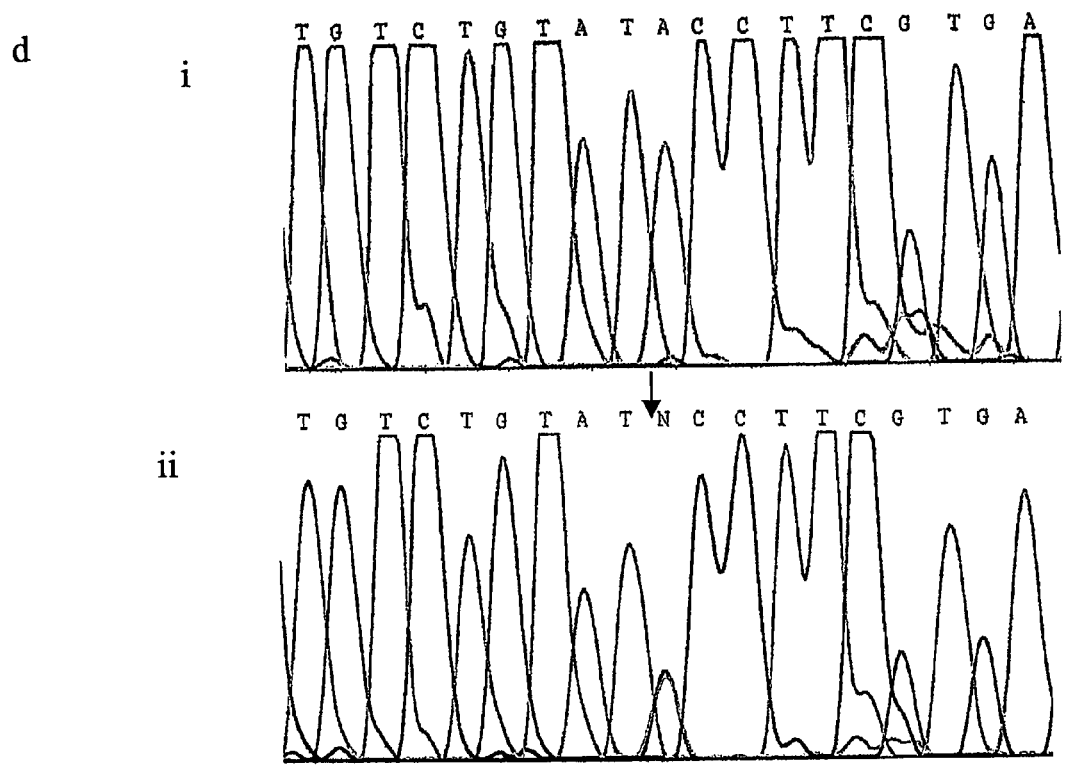
Figure 3:
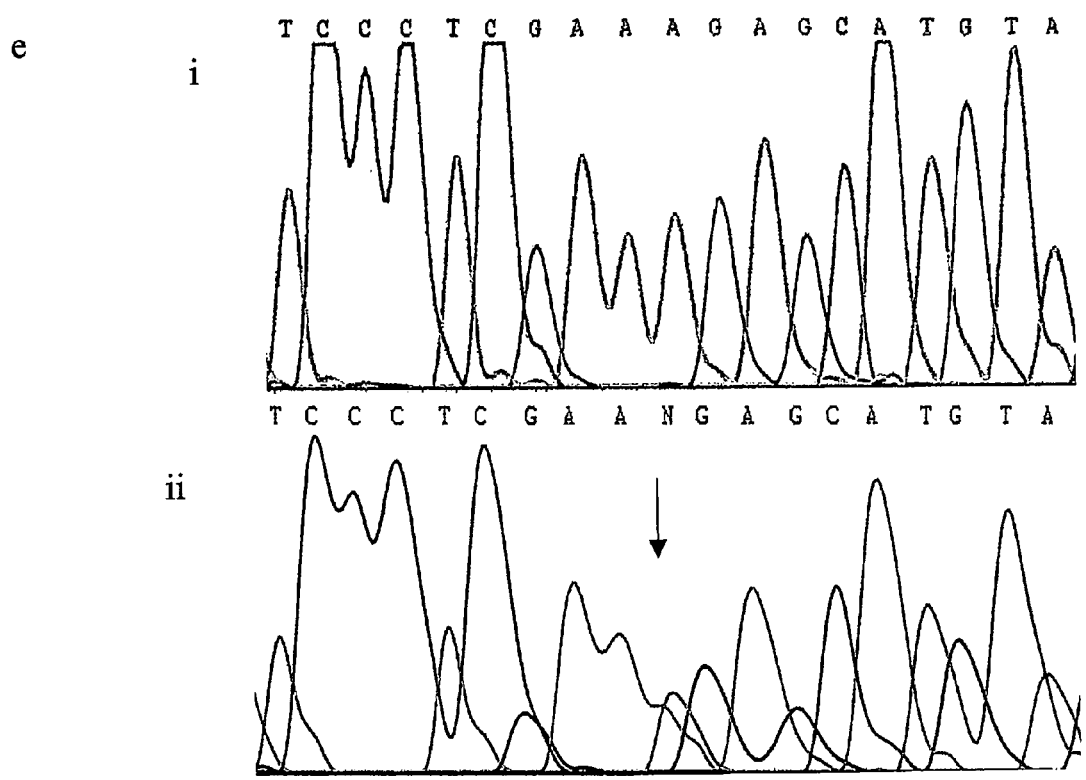
Figure 3:
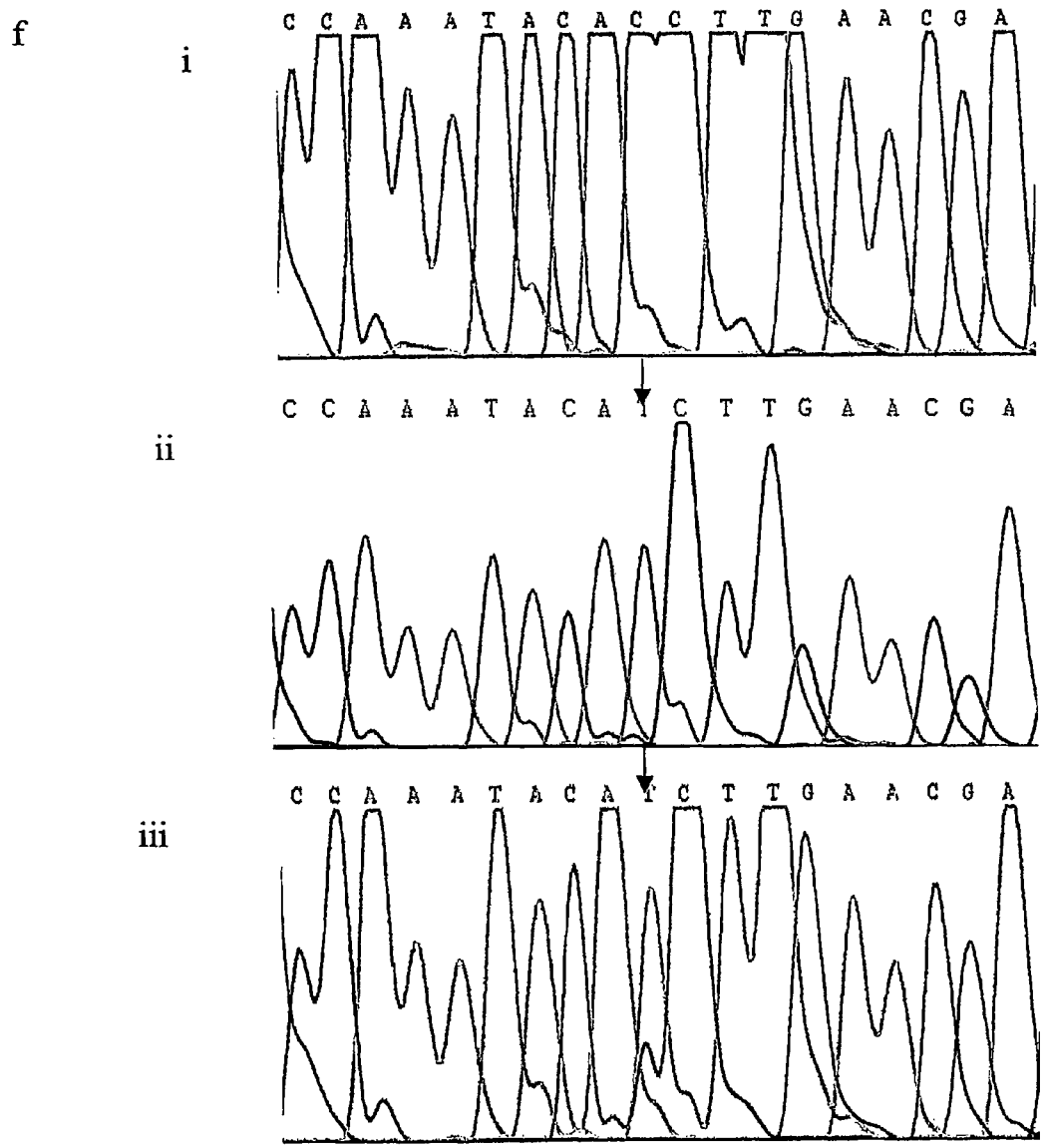
Figure 3:
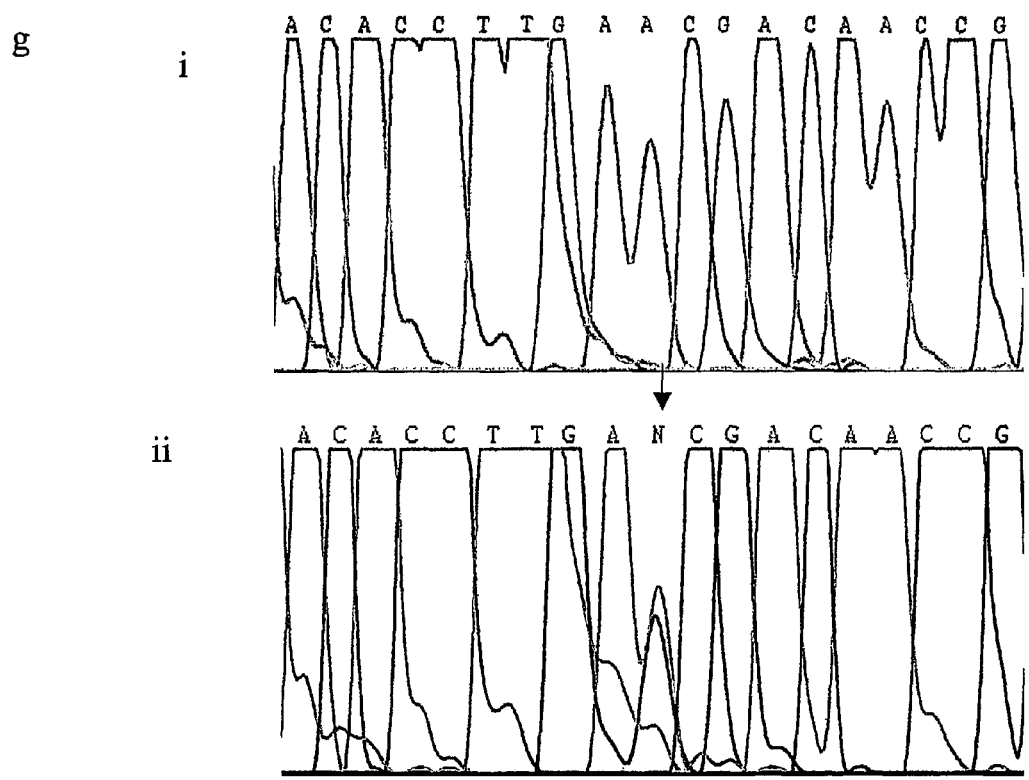
Figure 3:
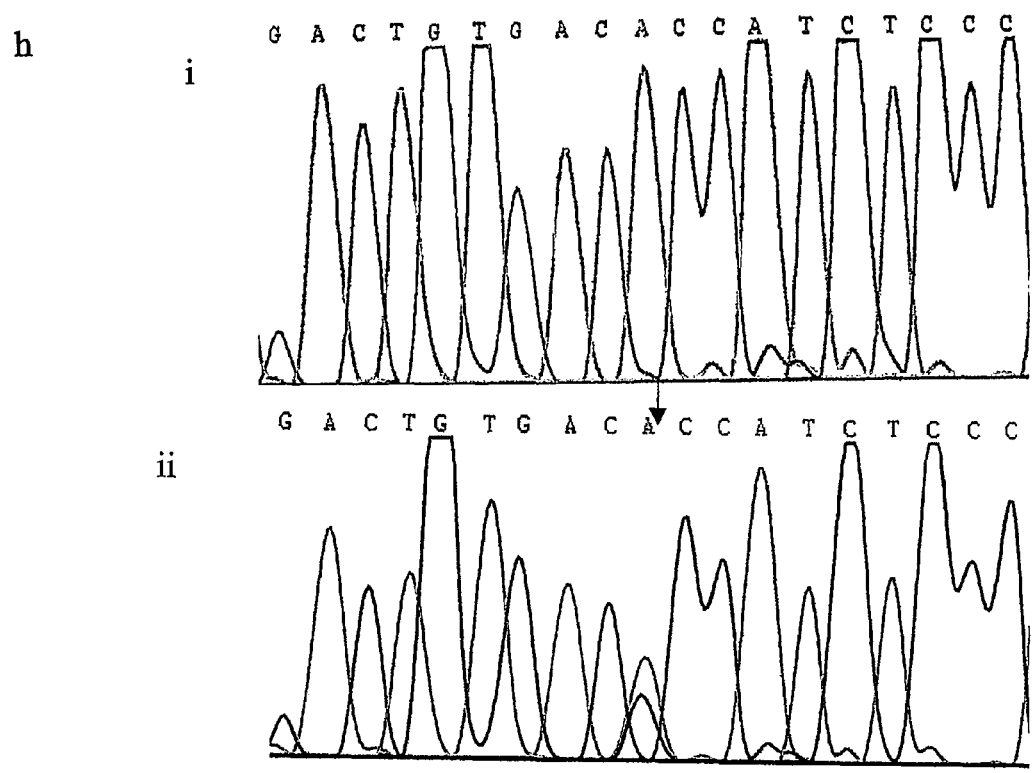
Figure 3:
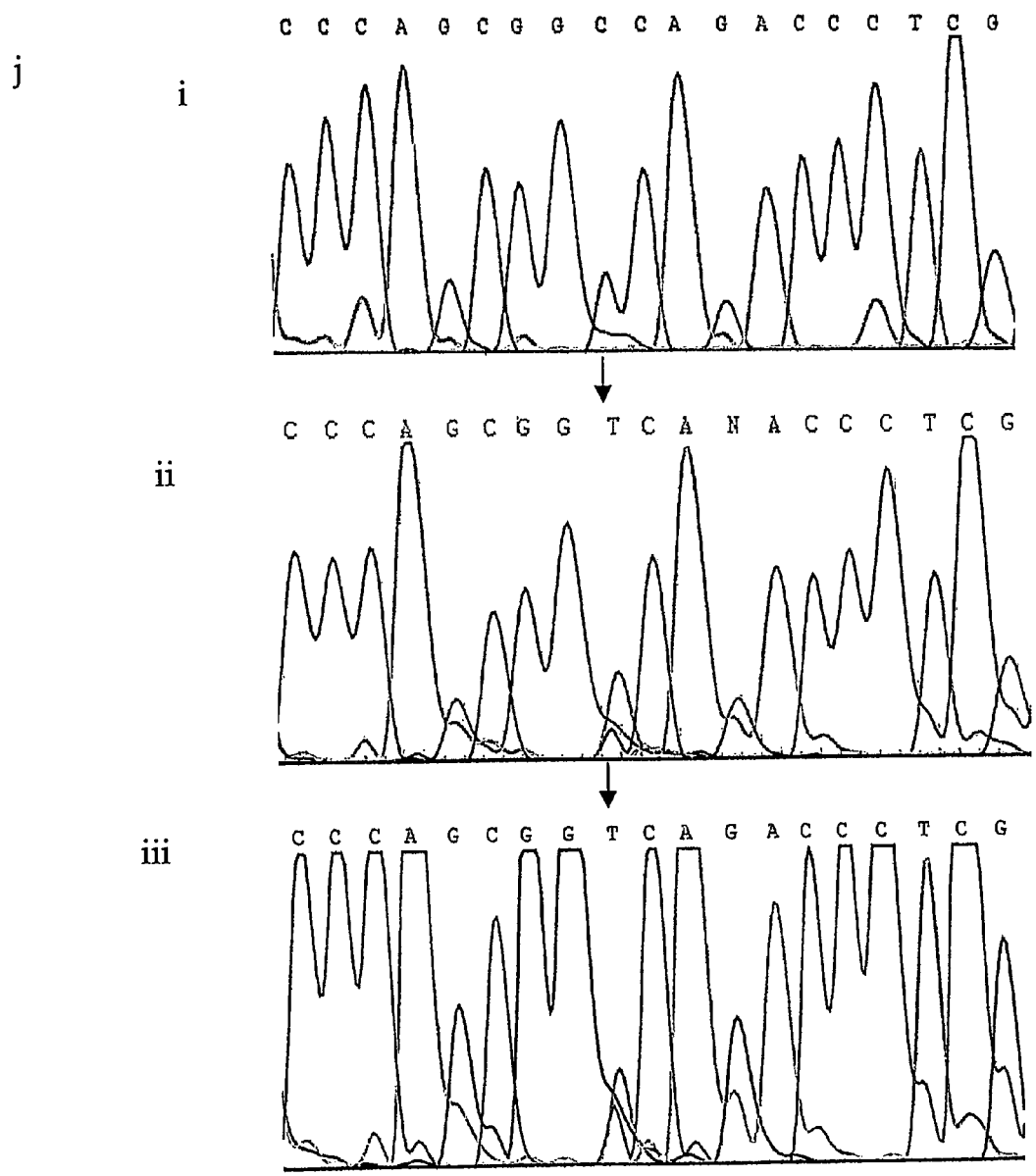
Figure 3:
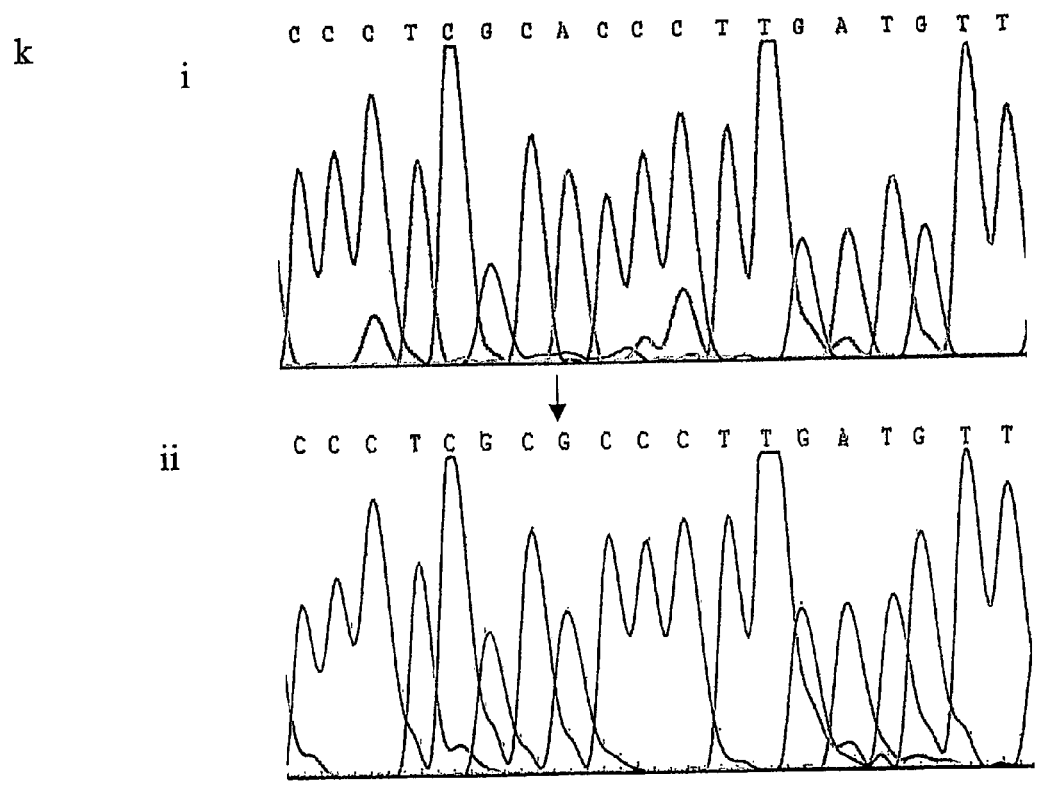
Figure 3:
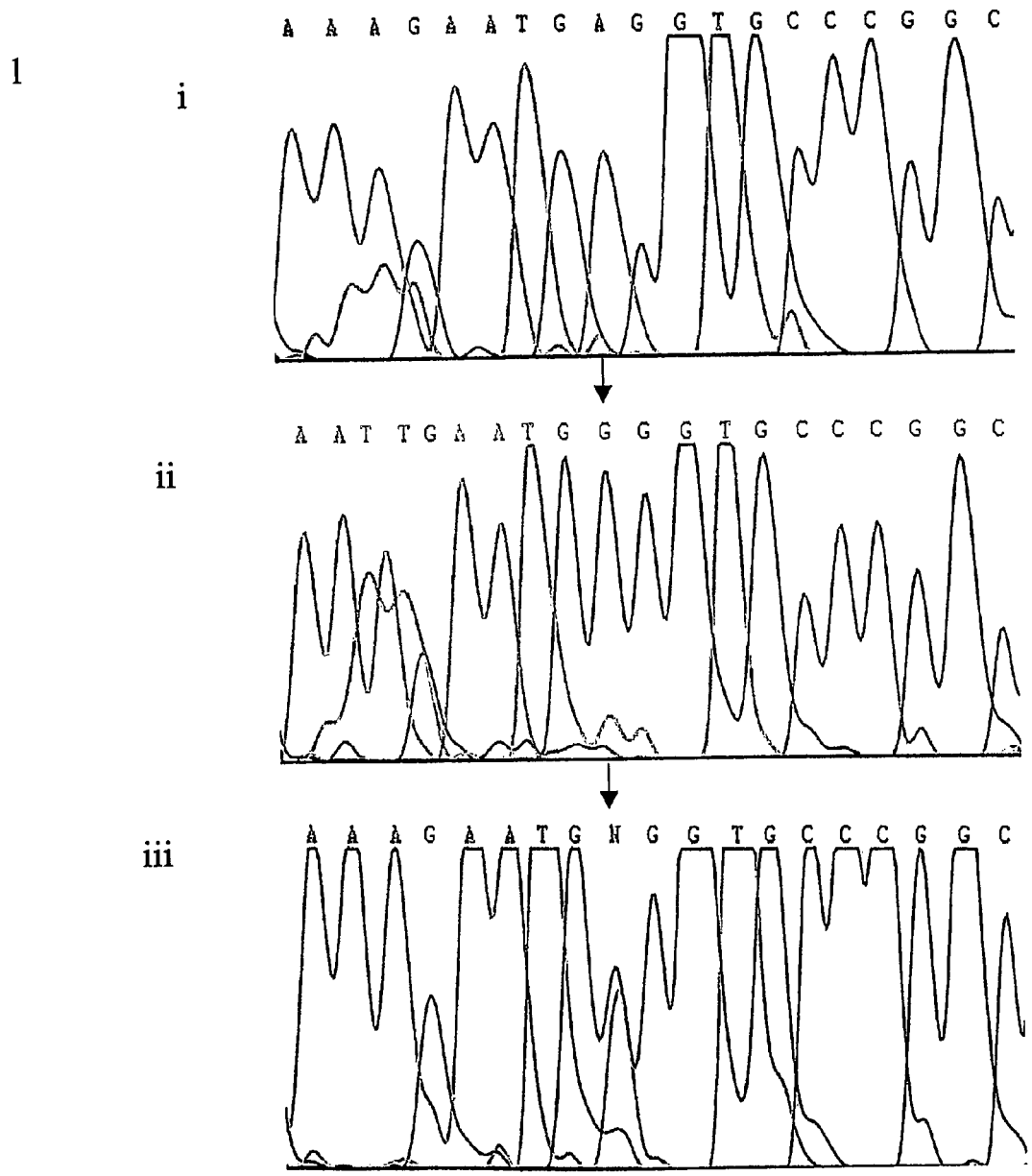
Figure 3:
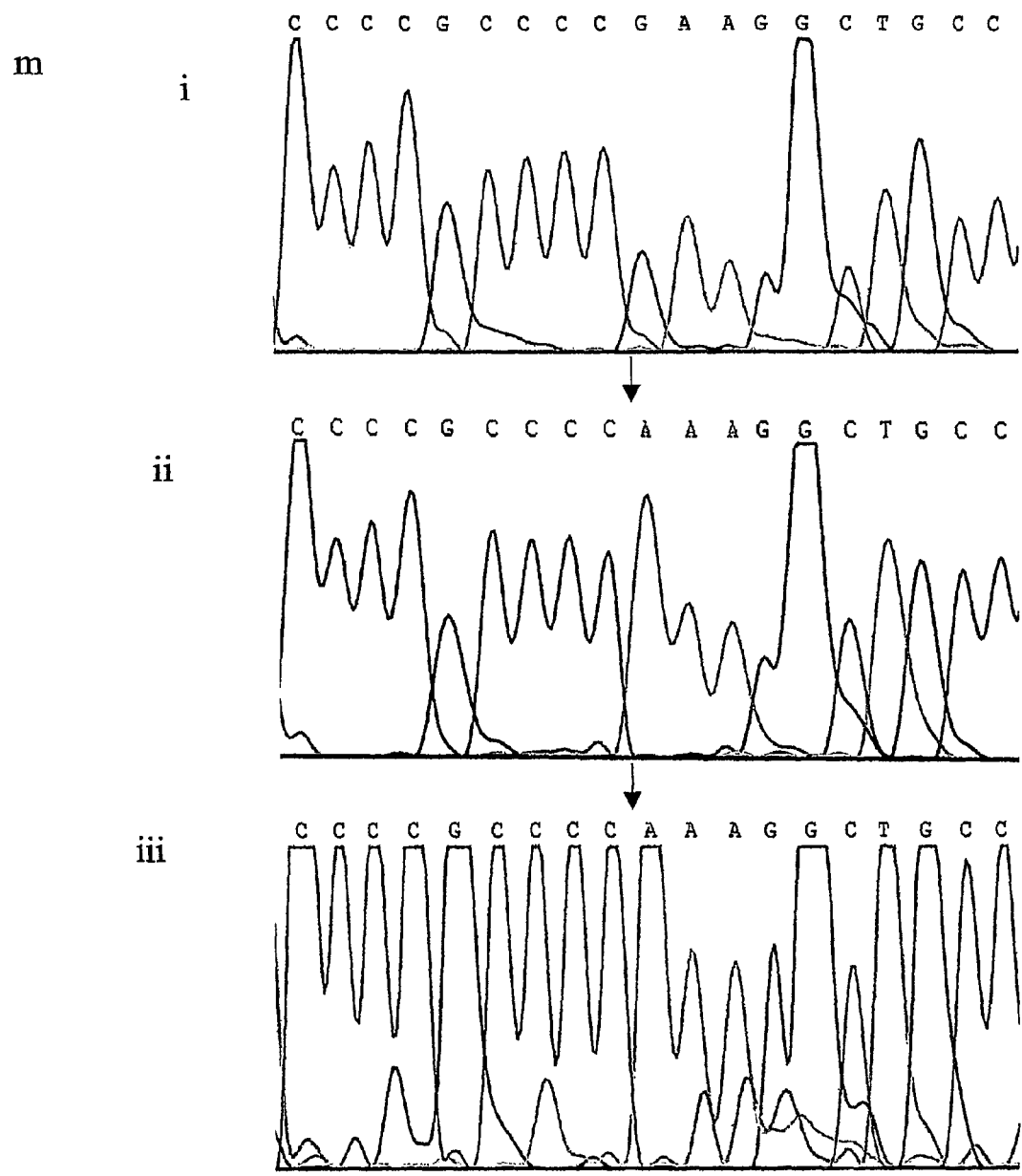

Additional Mutations 80 primary prostate tumours (including 10 of the 25 providing DNA for sequencing the mutation seen in LNCaP) and 11 prostate cancer metastases were screened for mutations in the cytoplasmic domain of the plexinB1 gene by SSCP analysis. Aberrant bands were excised from the gel and sequenced directly. 12 additional mis-sense mutations were identified (Table 1, FIG. 3).

Figure 4:
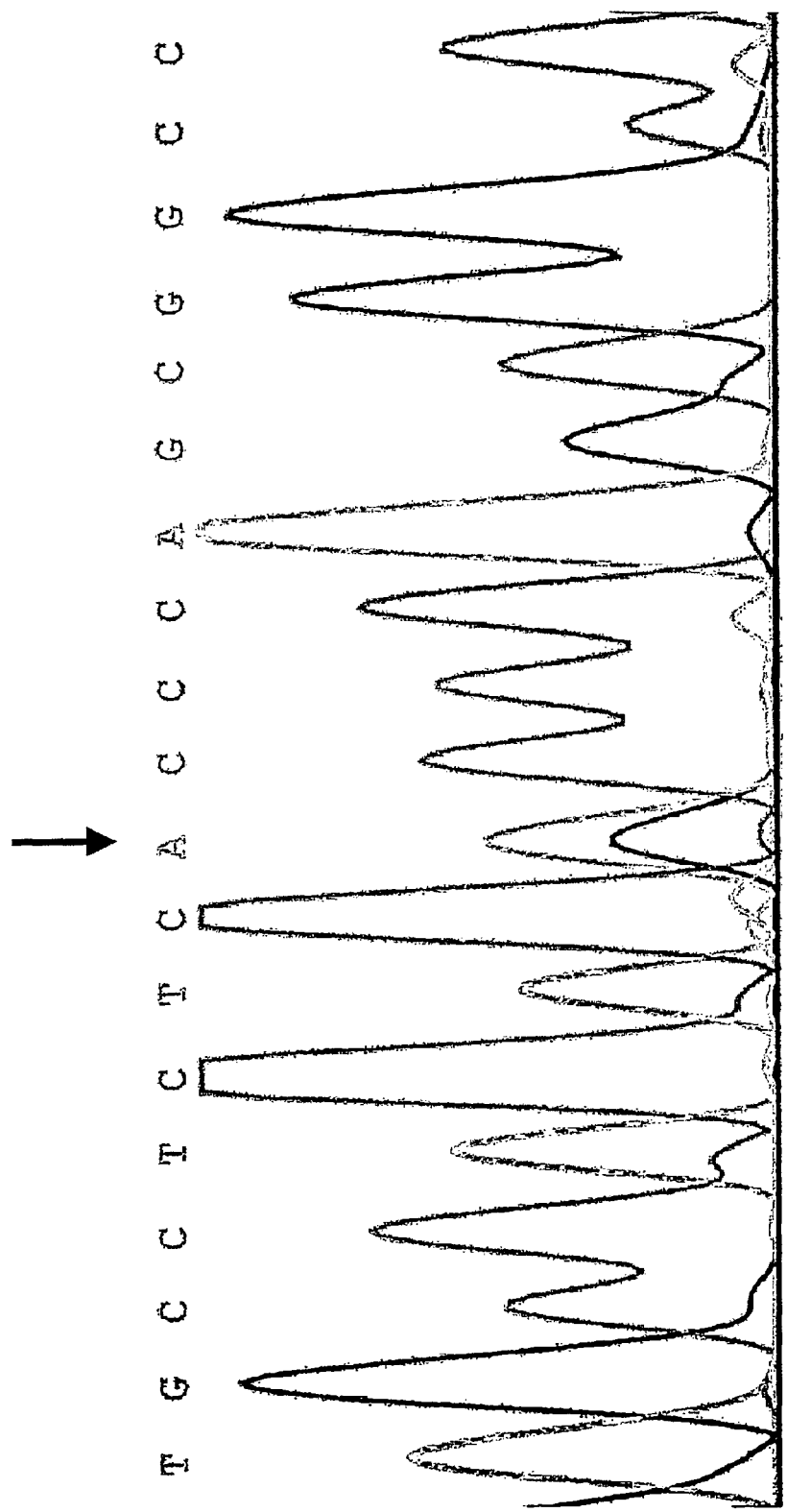
FIG. 4 shows the sequencing of PCR products from 7 primary prostate cancers. The arrow marks the position of the A5653G (Thr1795Ala) mutation (SEQ ID NO:16).

One of these mutations, A5653G, which potentially changes the threonine at position 1795 to an alanine, was found in 7/11 (64%) of metastases and 33/80 (41%) of primary cancers. The presence of the T1795A mutation was confirmed by direct sequencing of DNA from the metastases (FIG. 4) and by restriction enzyme digestion in the 33 primary tumours.

Figure 5:
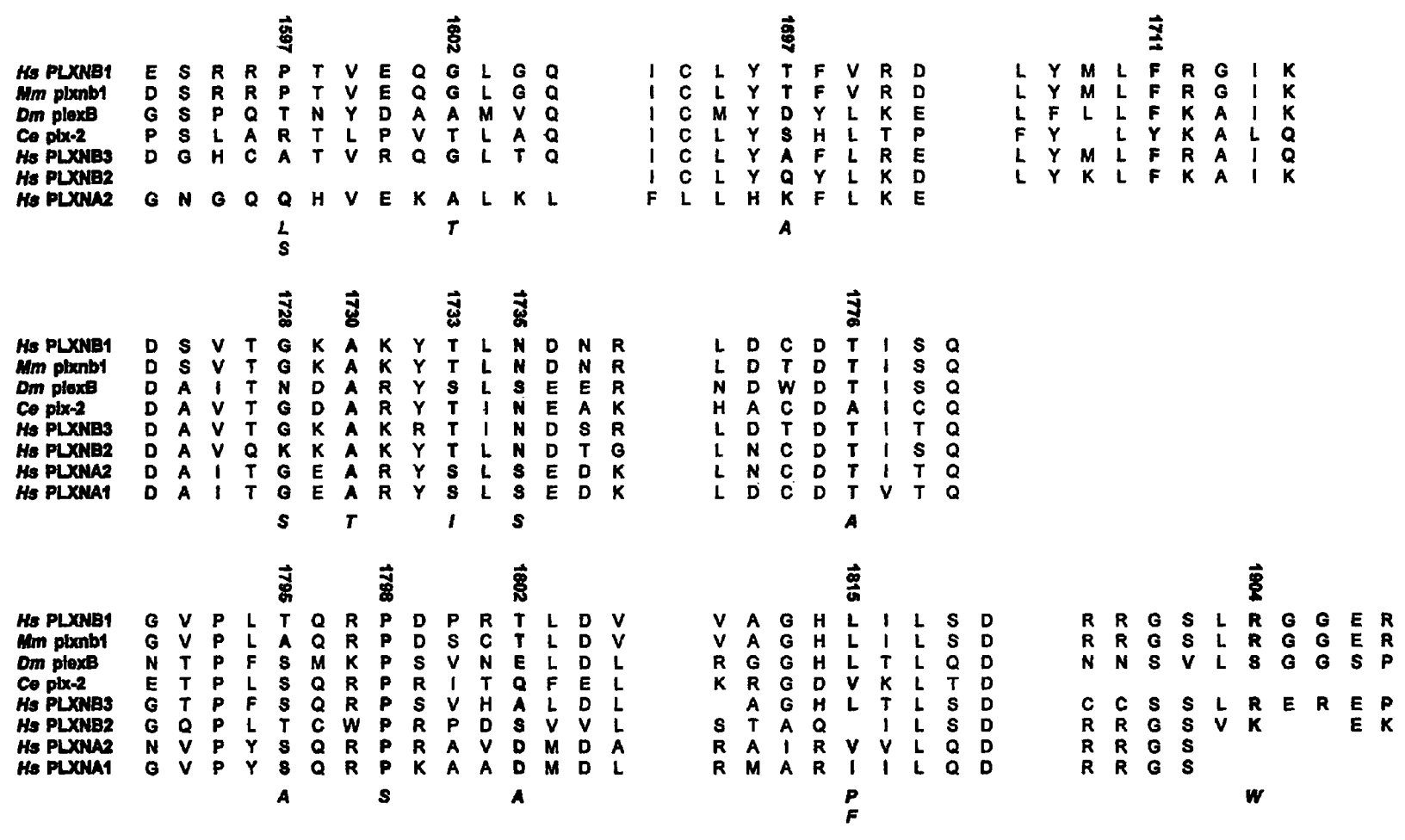

Position 1795 is part of a potential serine/threonine kinase phosphorylation site which is highly conserved in evolution. A threonine or serine is present at this position in the protein in mouse, Drosophila and C. elegans plexinB1 homologues as well as members of the other classes of the plexin family of proteins (plexins A1, A2, A3, B2, B3 and D1) (FIG. 5).

A T5714C sequence change, predicted to result in a change of amino acid from leucine 1815 to proline was found in 3 metastases. A leucine or valine in this position is conserved in plexinB1 homologues in other species and in other plexin family members (FIG. 5).

A C5060T mutation, which potentially changes proline 1597 to leucine, was also found in 3 metastases and a second mutation in a primary tumour (C5059T) changes the same amino acid to serine. A proline at this position in the protein is not conserved during evolution (FIG. 5)).

Six further mutations were identified in single metastases: G5074A (Gly1602T), T5468C (Thr1733Ile), A5474G (Asn1735Ser), C5662T (Pro1798Ser), A5674G (Thr1802Ala) and C5980T (Arg1904Trp). Thr1733 and Pro1798 are conserved in both A and B class plexins, while Gly1602, Asn1735, Arg1904 are conserved in class B plexins. Thr1802 is replaced with acidic amino acids in A class plexins which may mimic a phosphorylation site. Finally two mutations (F1711I and T1776A) were found in single primary tumours. Phe1711 is conserved in class B plexins and Thr1776 is conserved in class A and B plexins.

All 12 additional mutations were found to be absent from normal tissue of the same patient where available and are therefore somatic. The sequence changes were absent from at least 50 control individuals in every case.

The present findings show that mutation of the plexinB1 gene is associated with prostate cancer progression. The incidence of mutations was higher in prostate cancer metastases than primary tumours, with mutations in 91% of metastases (10/11) and 45% (36/80) of primary tumours. The metastases frequently contained multiple mutations. Three of the metastases each contained 3 mutations within this short stretch of the plexinB1 gene and 3 others contained two mutations. 8 of the mutations (L1815P in 3 tumours and P1798L in 3 tumours, T1802A and Pro1798Ser in one tumour each) occurred in addition to the common Thr1795Ala change. T1802A was found in the same SSCP band as the common (T1795A) mutation indicating that the two mutations are on the same allele. In contrast, only single mutations were found in primary tumours. In addition, the proportion of cells containing mutant plexinB1 was higher in metastases than primary tumour tissue. In one case where both primary and metastatic tissues were available from the same patient, the mutant allele was more highly represented in the metastases than the primary tumour. Together these results provide indication that mutations in the plexinB1 gene are selected for during cancer metastasis.

PlexinB1 Mutations in Breast Cancer 30 breast cancer lymph node metastases were screened for mutations in exons 22-29 of the plexin B1 gene by SSCP and 7 mutations were found in 6 cases (Table 2, FIG. 6). Three metastases had a T5059C sequence change, which is predicted to alter Pro1597 to Ser, and one metastasis had a mutation in the adjacent nucleotide (C5060T), which alters the same amino acid to Leu. Both these mutations were also observed in prostate cancer metastases. One breast cancer metastasis had the sequence change C1713T, which changes Leu1815 to Phe. Leu1815 was altered to Pro in 3 cases of prostate cancer metastasis. Two of the mutations were only found in breast cancer metastasis: G5452A (Gly1728Ser) and G5458A (Ala1730Thr). G5452A and C1713T were found in the same metastasis. These mutations were not present in 100 control chromosomes. These mutations were present at a low copy number in the lymph node metastasis.

TABLE 1

| Nucleotide | Amino acid | somatic+' | primary(95) | metastases(11) 1 | 2 | 3 | 4 | 5 | 6 | 7 | 8 | 9 | 10 | Total |
|---|---|---|---|---|---|---|---|---|---|---|---|---|---|---|
| C5060T | P1597L | x | | | x | x | | x | x | | | | | 4 |
| C5059T | P1597S | ND | 1 | | | | | | | | | | | 1 |
| G5074A | G1602T | x | | | | | | | x | | | | | 1 |
| A5359G* | T1697A* | x | 3 | | | | | | | | | | | 3 |
| T5401A | F1711I | ND | 1 | | | | | | | | | | | 1 |
| C5468T | T1733I | x | | | | | | | | x | | | | 1 |
| A5474G | N1735S | x | | | | | | | | x | | | | 1 |
| A5596G | T1776A | ND | 1 | | | | | | | | | | | 1 |
| A5653G | T1795A | x | 33 | x | x | x | x | x | | | x | x | | 40 |
| C5662T | P1798S | ND | | | | | | | | | | x | | 1 |
| A5674G | T1802A | x | | | | | x | | | | | | | 1 |
| T5714C | L1815P | x | | | x | | | x | | | x | | | 3 |
| C5980T | R1904W | ND | | | | | | | | | | | x | 1 |
| | | | (39/95 = 41%) | | | | | (10/11 = 91%) | | | | | | 59 |

*T1697A mutation was found in LNCaP and 3 primary tumours by direct sequencing
+'mutation absent from non cancer tissue from the same patient

TABLE 2

| Nucleotide | Amino acid | metastases(30) 1 | 2 | 3 | 4 | 5 | 6 | Total |
|---|---|---|---|---|---|---|---|---|
| T5059C | P1597S | x | x | x | | | | 3 |
| C5060T | P1597L | | | | x | | | 1 |
| C5713T | L1815F | | | | | x | | 1 |
| G5452A | G1728S | | | | | x | | 1 |
| G5458A | A1730T | | | | | x | | 1 |
| | | | | | | | | 7 |

The invention claimed is:

1. A method of identifying a compound as a putative anti-prostate cancer or anti-breast cancer agent, the method comprising;
determining the expression of a plexinB1 nucleic acid in a cell in the presence of a test compound as compared with expression of the plexinB1 nucleic acid in the cell in the absence of the test compound,
wherein said plexinB1 nucleic acid comprises of AB007867.1 (SEQ ID NO:112) with at least one mutation in the coding region of the nucleic acid selected from the group consisting of C5059T, C5060T, G5074A, A5359G, T5401A, G5452A, G5458A, C5468T, A5474G, A5596G, A5653G, C5662T, A5674G, C5713T, T5714C and C5980T, wherein the mutations are numbered starting at residue 1 of AB007867.1 (SEQ ID NO:112) and;
wherein a reduction in expression of the plexinB1 nucleic acid in the cell in the presence of the test compound as compared with expression of the plexinB1 nucleic acid in the cell in the absence of the test compound identifies the test compound as a putative anti-prostate cancer or anti-breast cancer agent.

2. The method of claim 1 wherein said at least one mutation is A5653G.

3. The method of claim 1 wherein said at least one mutation is C5059T or C5060T.

4. The method of claim 1 wherein said putative agent is an anti-breast cancer putative agent and said at least one mutation is G5452A or G5458A and a reduction in expression of the plexinB1 nucleic acid in the cell in the presence of the test compound as compared with expression of the plexinB1 nucleic acid in the cell in the absence of the test compound identifies the test compound as a putative anti-breast cancer agent.

5. The method of claim 1 wherein said putative agent is an anti-prostate cancer putative agent and said at least one mutation is A5653G and a reduction in expression of the plexinB1 nucleic acid in the cell in the presence of the test compound as compared with expression of the plexinB1 nucleic acid in the cell in the absence of the test compound identifies the test compound as a putative anti-prostate cancer agent.

* * * * *